(12) United States Patent
Keret et al.

(10) Patent No.: US 9,770,555 B2
(45) Date of Patent: Sep. 26, 2017

(54) COMPACT MEDICAL PUMP DEVICE

(71) Applicant: ToucheMedical, Ltd., Kiryat Bialik (IL)

(72) Inventors: Amir Keret, Kfar Vradim (IL); Zohar Man, Haifa (IL); Avihoo P. Keret, Atlit (IL)

(73) Assignee: ToucheMedical Ltd., Kiryat Bialik (IL)

( * ) Notice: Subject to any disclaimer, the term of this patent is extended or adjusted under 35 U.S.C. 154(b) by 976 days.

(21) Appl. No.: 13/961,650

(22) Filed: Aug. 7, 2013

(65) Prior Publication Data

US 2013/0324963 A1 Dec. 5, 2013

Related U.S. Application Data

(63) Continuation of application No. PCT/IL2012/050052, filed on Feb. 19, 2012.

(60) Provisional application No. 61/444,719, filed on Feb. 19, 2011.

(51) Int. Cl.
*A61M 5/172* (2006.01)
*A61M 5/142* (2006.01)
*A61M 5/145* (2006.01)

(52) U.S. Cl.
CPC ........ *A61M 5/172* (2013.01); *A61M 5/14244* (2013.01); *A61M 5/1452* (2013.01); *F04C 2270/0421* (2013.01); *Y10T 29/49826* (2015.01)

(58) Field of Classification Search
CPC .............. A61M 5/172; A61M 5/14244; A61M 5/1452; F04C 2270/0421; Y10T 29/49826
USPC ..... 604/65–67, 151, 131; 128/DIG. 1, 7, 12, 128/13
See application file for complete search history.

(56) References Cited

U.S. PATENT DOCUMENTS

| | | | |
|---|---|---|---|
| 2,185,992 A | | 1/1940 | Cady |
| 2,925,814 A | * | 2/1960 | Vibber ................... A61B 5/024 128/DIG. 7 |
| 3,923,060 A | * | 12/1975 | Ellinwood, Jr. ....... A61B 5/021 128/DIG. 1 |

(Continued)

FOREIGN PATENT DOCUMENTS

| | | |
|---|---|---|
| CN | 101622454 B | 1/2012 |
| DE | 19916252 | 11/2000 |

(Continued)

OTHER PUBLICATIONS

International Searching Authority: "International Preliminary Report on Patentability including Written Opinion of the International Searching Authority (PCT Rule 43bis.1)" for corresponding International Patent Application No. PCT/IL2012/050052; Date of issuance of report: Aug. 21, 2013.

(Continued)

*Primary Examiner* — Manuel Mendez
(74) *Attorney, Agent, or Firm* — M&B IP Analysts, LLC

(57) ABSTRACT

A compact medical fluid infusion pump and method for using thereof is described. The compact includes a medicament reservoir integrated with a rotary pump for providing a user thereof with a controlled quantity of fluid-medicament. The rotary pump includes at least one stationary arm and at least one rotating arm such that an operating device configured to operate the rotary pump thereby the fluid-medicament is impelled through an outlet channel of the reservoir and infusing the medicament into a user.

14 Claims, 19 Drawing Sheets

(56) References Cited

U.S. PATENT DOCUMENTS

| | | | |
|---|---|---|---|
| 3,936,214 | A | 2/1976 | Zupanick |
| 4,548,607 | A | 10/1985 | Harris |
| 5,399,074 | A | 3/1995 | Nose et al. |
| 5,578,012 | A | 11/1996 | Kamen et al. |
| 6,179,583 | B1 | 1/2001 | Weston |
| 6,283,949 | B1 | 9/2001 | Roorda |
| 6,726,678 | B1 | 4/2004 | Nelson et al. |
| 7,331,770 | B2 | 2/2008 | Oyaski |
| 7,614,857 | B2 | 11/2009 | Fuechslin et al. |
| 2004/0226962 | A1 | 11/2004 | Mazursky et al. |
| 2010/0280502 | A1 | 11/2010 | Hovind et al. |

FOREIGN PATENT DOCUMENTS

| | | |
|---|---|---|
| WO | 2006/027548 | 3/2006 |
| WO | 2008/002072 | 1/2008 |

OTHER PUBLICATIONS

International Search Authority: "International Search Report" for corresponding International Patent Application No. PCT/IL2012/050052; Date of Mailing: Sep. 24, 2012.
First Office Action, SIPO, Chinese Patent Application No. 2012800093768, Mailing No. 510627, Mar. 26, 2015.
Second Office Action, SIPO, Chinese Patent Application No. 201280009376.8, Mailing No. 510627, Dec. 14, 2015.

\* cited by examiner

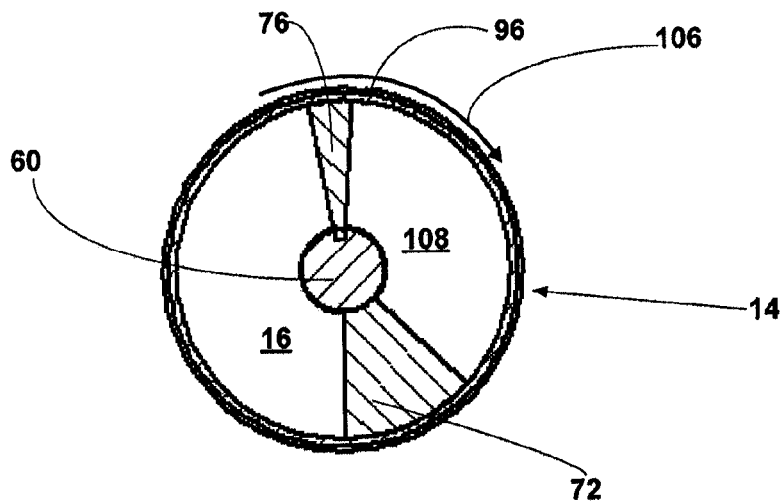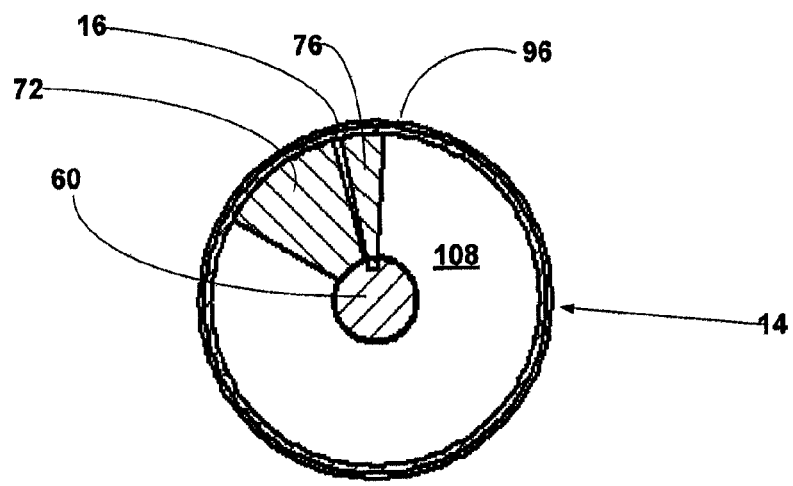

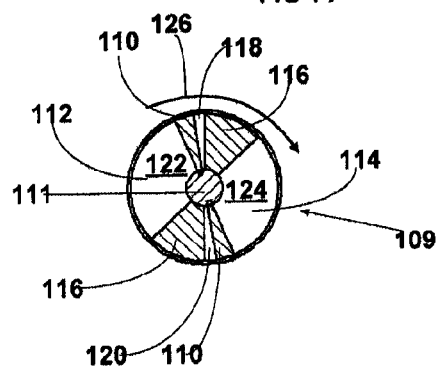
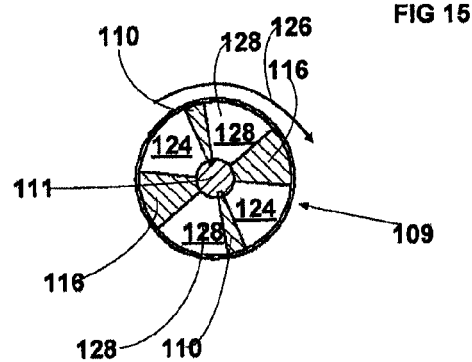
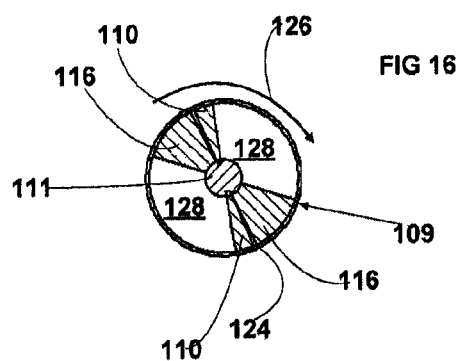

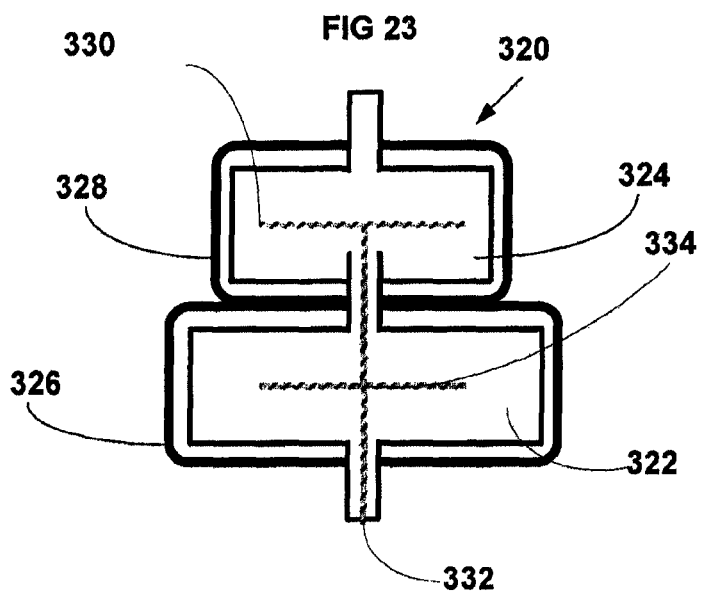
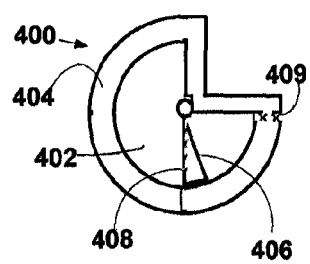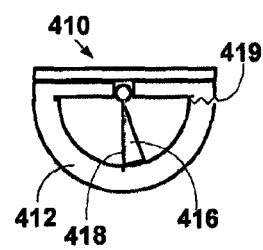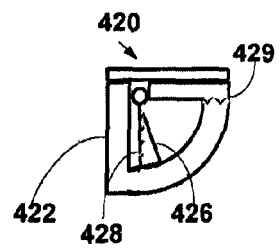

COMPACT MEDICAL PUMP DEVICE

CROSS-REFERENCE TO RELATED APPLICATIONS

This application is a continuation application of International application No. PCT/IL2012/050052 filed on Feb. 19, 2012 which claims the benefit of U.S. provisional patent application No. 61/444,719 filed on Feb. 19, 2011, the contents of which are incorporated herein by reference.

FIELD OF THE INVENTION

This invention relates to a compact medical pump device for controlled-infusion of at least one fluid-medicament into a user.

BACKGROUND OF THE INVENTION

Currently, a conventional needle syringe is typically used for infusing fluid medicaments into a user. The conventional syringe includes a fluid-medicament reservoir typically of cylindrical cross-section as well as a plunger member for injecting the fluid into the patient. Following insertion of the needle into the patient, the plunger member is depressed and the medicament is infused into the patient. Although the cylinder is typically graduated, the infusion process is not easily controllable and due to friction between the plunger and the cylindrical medicament holder, it is difficult to infuse accurate quantities of medicament into the user. However, there are maladies such as pain-relief, which require the infusion of exact quantities of medicaments, in order to maintain the health of the patient.

In addition, due to the cylindrical cross-section of the conventional syringe, portions of the medication are not injected into the patient and these portions remain inside the syringe. This causes wastage of the medicament.

Furthermore, due to the relatively large size of the conventional syringe device it is inconvenient for use in confined spaces. Additionally, if several medicaments are required to be injected into the patient, it is necessary for the medical personnel to remove the plunger from the syringe and refill the syringe cylinder with the new medicament and repeat the infusion process. Thus operation can be very uncomfortable and painful for the patient, who may remain with the needle inserted within his body, while the medical staff commences refilling the cylinder.

The following prior art is believed to be the current status of the art:

PCT Publication No. WO 2006/027548 describes a pump having an inlet port for connecting to a source and an outlet for supplying a pumped fluid. A rotor is rotatable within a pump housing and the inlet and the outlet ports are located around the path of the rotor within the housing.

German Patent No. DE 19916252 describes a low-volume fluid pump having a rotating shaft with a flat surface and including a fluid inlet port.

PCT Publication No. WO 2008/02072 describes an implantable delivery device including a fluid input port and a fluid output port.

U.S. Pat. No. 5,399,074 describes a centrifugal blood pump having a fluid input port and a fluid output port.

U.S. Pat. No. 5,578,012 describes a medical pump apparatus including a flexible diaphragm and a rotating vane disposed within a pumping chamber. A motor rotates a revolving hook which engages the drive rod within the pumping chamber. The pumping chamber includes an inlet for providing a fluid to the chamber and an outlet for tube for supplying the fluid to the patient.

U.S. Pat. No. 6,179,583 describes a metering device for pressurized liquids having a rotor including a free piston operating at right angles to a rotor axis. The rotor is retained within a stator having a fluid inlet port and a fluid outlet port.

U.S. Pat. No. 7,331,770 describes a disposable device for treatment and promoting healing of damaged body tissue. The device includes two fluid pumps. The first pump includes a fluid inlet port and a fluid outlet port. The first pump pumps a first fluid and the second pump pumps a second fluid.

U.S. Pat. No. 7,614,857 describes a medical pump including a rotary pump having an inlet and outlet.

The cited prior art describes prior art pumps having a fluid input port. The prior art pumps do not include a reservoir for storing the fluid to be pumped contained within the pump.

US Published Patent Application No. 2010/0280502 describes a medical pump including a reservoir for storing a fluid-medicament. In the prior art device, the fluid is pumped into an outlet of the device by the action of a moving piston.

This prior art describes a medical pump which includes a piston for supplying the fluid-medicament to a patient.

SUMMARY OF THE INVENTION

The present invention presents a compact medical pump device for medicament-infusion of at least one fluid-medicament into a user under controlled conditions, so that a user thereof is able to receive a predetermined dosage of the at least one medicament, in accordance with medical requirements. In addition, in the present invention, the fluid-medicament is contained within a fluid reservoir which is integrated and self-contained within a fluid pump device, where the pump is a rotary fluid pump. Following use of the reservoir, the reservoir is detached from the pump and disposed thereof and a replacement reservoir of medicament is inserted into the pump device.

The compact medical pump is attached to the body of the user at the requisite body location by means, such as sticky paper and/or Velcro™ pad.

The present invention also includes a controlled drive mechanism configured to operate a rotary pump so as to controllably discharge the medicament from the medicament reservoir. The operation of the rotary pump is controlled by a remote controller and the instructions are forwarded wirelessly to the pump device by, for example, EM signals or by acoustic signals. Additionally or alternatively, a pump controller is attached to the pump device and located on the user, and control of the pump device is conducted, for example, by wire. Thus, the user of present invention is able to control the infusion of the fluid medicament, in accordance to the medical requirements, to infuse an accurate quantity of the at least one medicament over a required time interval.

Due to the rotary motions of the pump's members, a smooth and electronically controlled pumping action is achieved instead of an irregular movement of the plunger of the conventional syringe due to the irregular movement of the user/medical staff performing the infusion.

The present invention overcomes the shortcomings and problems of the conventional syringe and the prior art devices, and presents a compact infusion device, whose operation is electronically controlled. In addition, the user and/or medical staff typically applies the medical requirements to the pump device, such as time interval for infusion and fluid flow rate by means of a remote controller, which transmits the pumping conditions to an electronic controller located, for example, internally in the pump housing.

Typical dimensions of the conventional syringe with those of the present invention: A conventional syringe has an internal diameter of cylindrical cross-section is approximately 0.5 cms and with a withdrawn plunger, the length of the syringe is approximately 20 cms. Inserting the plunger, the length of the syringe is reduced to approximately 10 cms. A typical fluid capacity of a conventional syringe 2 cc. The compact infusion pump of the present invention includes a height, H, of internal section of pump (FIG. 10A) 0.5 cms., a diameter, D, (FIG. 10A) 2.5 cms., with a typical fluid capacity 2 cc.

Thus, the present invention includes a smaller and compact infusion device for storing and infusing similar quantities of medicament, in comparison with the conventional syringe.

The present invention is compact, permitting it to be attached to the patient's body, by means, such as sticky paper and/or as a Velcro™ strap. The present invention is attached to the patient's body and does not require removing therefrom when changing the infusing medicaments. In addition, the present invention permits storage of more than one medicament, thus it is possible to infuse more than one medicament without replacing the pump device and the user undergoing repeated discomfort and pain due to the replacement of the syringe's reservoir.

The infusion process of the present invention is controlled by a controller unit, thus allowing the patient to receive accurately controlled amounts of medicament in accordance with medical requirements, at pre-prescribed times. In addition, using the present device, the patient is able to receive concomitantly controlled amounts of more than one medicament in accordance with medical requirements.

The various elements of the pump device are manufactured without a parting line, thus ensuring a smooth connection and no-leakage between the various elements of the pump device as well as the integrity and intactness of the present invention.

In accordance with a preferred embodiment of the present invention a compact medical fluid infusion pump including a medicament reservoir integrated with a rotary pump and configured to contain a fluid-medicament, the rotary pump includes at least one stationary arm and at least one rotating arm and an operating device configured to operate the rotary pump. The operating device is configured to rotate the rotating arm relative to the at least one stationary arm such that the medicament is impelled through an outlet channel of the reservoir and infusing the medicament into a user.

Further in accordance with a preferred embodiment of the present invention, the at least one stationary arm includes a proximal end and a distal end, the proximal end is attached to a central axle of the reservoir and the distal end abuts an outer wall of the reservoir.

Still further in accordance with a preferred embodiment of the present invention, the rotating arm includes a proximal end and a distal end and wherein the proximal end abuts the central axle and the distal end is attached to the outer wall.

Additionally in accordance with a preferred embodiment of the present invention the outlet channel is located within the at least one stationary arm attached and the outlet channel is located within the at least one rotating arm attached.

Further in accordance with a preferred embodiment of the present invention the operating device includes a mechanical drive mechanism.

Still further in accordance with a preferred embodiment of the present invention, the operating device includes a manual operating mechanism.

Preferably, the drive mechanism is mechanically coupled to the reservoir and rotates the reservoir about the central axle thereby impelling the fluid out of the reservoir. The drive mechanism is mechanically coupled to the central axle and rotates the at least one rotating arm within the reservoir thereby impelling the fluid out of the reservoir.

Additionally in accordance with a preferred embodiment of the present invention the reservoir includes a replacement air input channel thereby replacement air flows into the reservoir to replace the dispensed medicament.

Further in accordance with a preferred embodiment of the present invention the reservoir has a spherical-contoured outer wall.

Preferably, the reservoir has an ellipsoidal-contoured outer wall.

Further in accordance with a preferred embodiment of the present invention the compact fluid pump includes a medicament outlet fluidly coupled to a syringe needle for infusing the medicament into the user.

Further in accordance with a preferred embodiment of the present invention the compact infusion pump further including a controller adapted to control dispensing of the at least one predetermined dosage of the at least one fluid-medicament through the medicament outlet.

The reservoir is disposable, detachable and reusable.

In accordance with another preferred embodiment of the present invention, a compact fluid infusion pump for infusing at least one fluid-medicament into a user including a housing, a medicament reservoir located within the housing, configured to contain the at least one fluid-medicament and including a medicament outlet. The drive mechanism is configured to operate the pump thereby impelling at least one predetermined dosage of the at least one fluid-medicament out of the reservoir and infusing the at least one predetermined dosage of the at least one fluid-medicament into the user via the medicament outlet.

Further in accordance with a preferred embodiment of the present invention the drive mechanism is coupled to an outer wall of the medicament reservoir, thereby rotating the reservoir about a central axis of the housing.

Still further in accordance with a preferred embodiment of the present invention the reservoir includes: at least one stationary arm, including a proximal end attached to the central axle, a contoured distal end abutting an outer wall the reservoir and at least one medicament channel located within the stationary arm and fluidly coupled to the medicament outlet.

Additionally in accordance with a preferred embodiment of the present invention the reservoir further includes: at least one rotating arm, including: a contoured proximal end abutting the central axle and a distal end attached the outer wall of the reservoir. By rotating the reservoir the at least one rotating arm impels the at least one predetermined dosage of the at least one fluid-medicament through the at least one medicament channel and into the outlet.

Further in accordance with a preferred embodiment of the present invention the drive mechanism is coupled to a central axle of the reservoir thereby rotating the central axle of the medicament reservoir and maintaining the reservoir stationary.

Additionally in accordance with a preferred embodiment of the present invention the reservoir includes: at least one stationary arm, including: a proximal end attached to the central axle, and a contoured distal end abutting an outer wall of the reservoir.

Still further in accordance with a preferred embodiment of the present invention the reservoir further includes: at least one rotating arm, including: a contoured proximal end abutting the center axle, a distal end attached to the outer wall of the reservoir; at least one medicament channel located within the rotating arm and fluidly coupled to the medicament outlet. By rotating the central axis the at least one stationary arm impels the at least one predetermined dosage of the at least one fluid-medicament through the at least one medicament channel and into the medicament channel.

Further in accordance with a preferred embodiment of the present invention the compact pump includes a controller adapted to control dispensing of the at least one predetermined dosage of the at least one fluid-medicament. Preferably, the controller is remote from the fluid infusion pump or the controller is attached to the fluid infusion pump. Alternatively, the controller is located within the fluid infusion pump.

Further in accordance with a preferred embodiment of the present invention the controller is adapted to control a fluid infusion rate of the at least one fluid-medicament into the circulatory system of the user, a fluid infusion rate of the at least one fluid-medicament subcutaneously into the user.

Further in accordance with a preferred embodiment of the present invention the drive mechanism includes a power supply, a motor and a gear mechanism mechanically coupled to the motor by means of a drive shaft. The drive mechanism includes a mechanical drive mechanism and/or an electromechanical drive mechanism.

Additionally in accordance with a preferred embodiment of the present invention the medicament reservoir includes an encoder for determining an angular rotation of the medicament reservoir and/or the central axle.

Further in accordance with a preferred embodiment of the present invention a quantity of the infused at least one fluid-medicament.

Still further in accordance with a preferred embodiment of the present invention the encoder determines a quantity of infused at least one fluid-medicament and an infusion time interval thereby determining a fluid flow rate of the at least one fluid medicament.

Furthermore, the reservoir further includes graduation marks the graduation marks are selected from the group consisting of optical marks, magnetic marks, number of teeth of the gear mechanism, induction marks and/or any combination thereof.

Further in accordance with a preferred embodiment of the present invention the encoder further includes a reading head for reading the graduation marks and determining the angular rotation of the reservoir, the reading head is selected from the group consisting of an optical reading head, a magnetic reading head, an induction reading head and any combination thereof.

Additionally in accordance with a preferred embodiment of the present invention the encoder determines a blockage in the medicament outlet and/or the encoder determines an electromechanical failure in the drive mechanism.

Further in accordance with a preferred embodiment of the present invention the reservoir further includes at least one air inlet port for inflow of replacement air to replace an infused quantity of at least one fluid-medicament ejected from the infusion pump.

Further in accordance with a preferred embodiment of the present invention the central axle is coated with a sealant thereby preventing leakage of the fluid between the at least one stationary arm and the at least one rotating arm. Typically, the sealant materials include rubber, Silicone rubber, polymerized siloxanes and/or polysiloxanes, such as WKT and Polydimethylsiloxane and/or any combination thereof.

Still further in accordance with a preferred embodiment of the present invention the at least one stationary arm includes a smooth contoured distal end thereby enabling an uninterrupted rotation of the reservoir about the central axle and the at least one rotating arm includes a smooth contoured proximal end thereby enabling an uninterrupted rotation of the reservoir about the central axle.

There is provided in accordance with yet another preferred embodiment of the present invention a compact fluid infusion pump for infusing at least one fluid-medicament into a user including: a housing, a medicament reservoir located within the housing, including: a central axle, at least one stationary arm extending through the central axle and partitioning the reservoir into at least two compartments, each one of the at least two compartments is configured to contain the at least one fluid-medicament, and at least one fluid-medicament outlet fluidly coupled to the each one of the at least two compartments, and a drive mechanism. The drive mechanism is configured to operate the pump thereby impelling at least one first predetermined dosage of the at least one fluid-medicament out of a first compartment and at least one second predetermined dosage of the at least one fluid-medicament out of a second compartment and infusing the first and second dosages into the user via the medicament outlet.

Further in accordance with a preferred embodiment of the present invention the reservoir further includes: at least one rotating arm extending through the central axle, including: a contoured proximal end abutting attached to the central axle, a distal end attached to an outer wall the reservoir, and a medicament channel fluidly coupled to the medicament outlet. By rotating the reservoir the rotating arm impels the at least one first predetermined dosage and the at least one second predetermined dosage into the medicament channel.

Further in accordance with a preferred embodiment of the present invention the first compartment and the second compartment include equal fluid capacities. Alternatively, the first compartment and the second compartment have unequal fluid capacities.

In accordance with yet a further embodiment of the present invention, a compact fluid infusion pump for infusing at least one fluid-medicament into a user including: a housing; a medicament reservoir located within the housing and including at least two stacked reservoirs, each one of the at least two compartments is configured to contain at least one fluid-medicament, and a drive mechanism. The drive mechanism is configured to operate the pump thereby impelling a predetermined dosage of the at least one fluid-medicament out of one of the at least two stacked reservoirs into the user via the medicament outlet.

Further in accordance with a preferred embodiment of the present invention the at least one of the at least two stacked reservoirs includes: at least one rotating arm located, including: a contoured proximal end abutting the central axle, a distal end attached to an outer wall the lower reservoir, at least one medicament channel fluidly coupled to the medicament outlet. By rotating the at least one of the at least two reservoirs the predetermined dosage is impelled through into the at least one medicament channel.

Additionally in accordance with a preferred embodiment of the present invention, each one of the at least two stacked reservoirs include equal capacities of the fluid-medicaments.

Still further in accordance with a preferred embodiment of the present invention each one of the at least two stacked reservoirs include unequal capacities of the fluid-medicaments.

Further in accordance with a preferred embodiment of the present invention the central axle is coated with a sealant thereby preventing leakage of the fluid between the at least one stationary arm and the at least one rotating arm. Typically, the sealant materials includes materials includes rubber, Silicone rubber, polymerized siloxanes and/or polysiloxanes, such as WKT and Polydimethylsiloxane.

Still further in accordance with a preferred embodiment of the present invention the at least one stationary arm includes a smooth contoured distal end thereby enabling an uninterrupted rotation of the reservoir about the central axle and the at least one rotating arm includes a smooth contoured proximal end thereby enabling an uninterrupted rotation of the reservoir about the central axle.

The reservoir is disposable, detachable and reusable.

There is provided in accordance with a further preferred embodiment of the present invention, a method for infusing at least one fluid-medicament into a patient including: providing a compact fluid infusion pump, integrating a fluid medicament reservoir with the fluid pump, selecting a control application according to predetermined medical requirements on a remote control unit the remote control unit in communications a controller located in the compact pump, selecting a unique pairing mechanism on the remote control unit enabling communications between the remote control unit and the compact pump, communicating the selected application to the pump, receiving the application at the controller and activating the pump, and operating the pump so as to enable an infusion of the medicament into a patient.

Further in accordance with a preferred embodiment of the present invention the checking a rotation angle of the reservoir by an encoder to determine if the required quantity of medicament has been administered to the patient.

There is provided in accordance with a preferred embodiment of the present invention a compact fluid infusion pump including: a fluid reservoir integrated with a rotary pump and containing a fluid, the rotary pump includes at least one stationary arm and at least one rotating arm, and an operating device configured to operate the rotary pump. The operating device is configured to rotate the rotating arm relative to the at least one stationary arm such that the fluid is impelled through an outlet channel of the reservoir and into a fluid outlet.

Further in accordance with a preferred embodiment of the present invention the at least one stationary arm includes a proximal end and a distal end, the proximal end is attached to a central axle of the reservoir and the distal end abuts an outer wall of the reservoir.

Still further in accordance with a preferred embodiment of the present invention the rotating arm includes a proximal end and a distal end and wherein the proximal end abuts the central axle and the distal end is attached to the outer wall.

Additionally in accordance with a preferred embodiment of the present invention the outlet channel is located within the at least one stationary arm attached.

Further in accordance with a preferred embodiment of the present invention the outlet channel is located within the at least one rotating arm attached.

Further in accordance with a preferred embodiment of the present invention the operating device includes a mechanical drive mechanism.

Still further in accordance with a preferred embodiment of the present invention the operating device includes a manual operating mechanism.

Additionally in accordance with a preferred embodiment of the present invention the reservoir includes a replacement air input channel thereby replacement air flows into the reservoir to replace the dispensed medicament.

Further in accordance with a preferred embodiment of the present invention the drive mechanism is mechanically coupled to the reservoir and rotates the reservoir about the central axle thereby impelling the fluid out of the reservoir.

Further in accordance with a preferred embodiment of the present invention the reservoir has a spherical-contoured outer wall.

Additionally in accordance with a preferred embodiment of the present invention the reservoir has an ellipsoidal-contoured outer wall.

Further in accordance with a preferred embodiment of the present invention the drive mechanism is mechanically coupled to the central axle and rotates the at least one rotating arm within the reservoir thereby impelling the fluid out of the reservoir.

Additionally, in accordance with a preferred embodiment of the present invention the including a controller adapted to control dispensing of the at least one predetermined dosage of the at least one fluid through the fluid outlet.

The reservoir is disposable, detachable and reusable.

There is provided in accordance with another preferred embodiment of the present invention, a method of assembling a compact fluid infusion pump comprising: providing a first portion of a semi-circular leakage-proof fluid reservoir having a contoured outer wall and an upper cutout and a lower cutout, providing a second portion of a semi-circular leakage-proof fluid reservoir having a contoured outer wall and an upper cutout and a lower cutout, providing at least two stationary arms rotating arms and attaching said stationary arms to a contoured central axle, inserting said central axle and at least two stationary arms into by inserting said central axle into said upper cutout and said lower cutout located in said first portion, inserting a first stationary arm into said first portion, rotating a second stationary arm into said second portion and bonding said first and said second portions.

Further in accordance with a preferred embodiment of the present invention, central axle, said first stationary and said second stationary are coated with a compressible sealant material on said central axle. The sealant material is selected from the group consisting of rubber, Silicone rubber, polymerized siloxanes, polysiloxanes, WKT, Polydimethylsiloxane and any combination thereof.

It is appreciated that the present invention has additional non-medical applications, which also require accurately controlled insertion of fluid into a device or system. For such uses, the current pump device is fluidly coupled to an inlet port of the device and the infusion process proceeds.

BRIEF DESCRIPTION OF THE DRAWINGS

A preferred embodiment of the current invention is described hereinbelow with reference to the following drawings:

FIG. 12 shows the locations of the rotating arm and the stationary arm for a partially empty reservoir, in accordance with a preferred embodiment of the present invention;

FIG. 13 shows an end-of-travel location of the rotating arm and the stationary arm for an empty reservoir, in accordance with a preferred embodiment of the present invention;

FIG. 14 presents a view of the reservoir including, inter alia, the rotating and stationary arms extend diametrically through a central axle and partitions the reservoir into at least two compartments, in accordance with another preferred embodiment of the present invention;

FIG. 15 shows the locations of the diametrically rotating and stationary arms in which the reservoir is partially empty, in accordance with another preferred embodiment of the present invention;

FIG. 16 shows the locations of the diametrically rotating and stationary arms in which the reservoir is empty, in accordance with another preferred embodiment of the present invention;

FIG. 23 presents a side-view of a stacked reservoir with at least two compartments having unequal fluid capacities; in accordance with another preferred embodiment of the present invention;

FIGS. 24A, 24B and 24C show reservoirs having different wall geometries, in accordance with yet a further preferred embodiment of the invention.

DETAILED DESCRIPTION OF PREFERRED EMBODIMENTS OF THE PRESENT INVENTION

Figure 1:
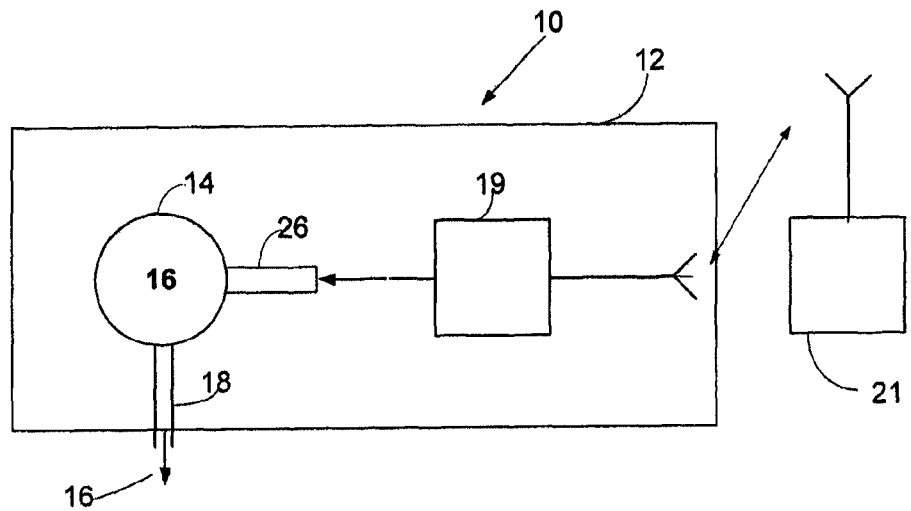
FIG. 1 shows a fluid infusion pump device for infusing at least one fluid-medicament into a user, in accordance with a preferred embodiment of the present invention.

Reference is now made to FIG. 1, which shows a fluid infusion pump device 10 for infusing at least one fluid-medicament to a user, in accordance with a preferred embodiment of the present invention. The infusion pump device 10 includes, inter alia, a housing 12 and a detachable and disposable reservoir 14 located therein and containing at least one fluid-medicament 16. The infusion pump device 10 operates as a rotary pump with the fluid reservoir 14 located therein. The reservoir 14 is mechanically coupled to a drive mechanism 26, as described below. A medicament outlet conduit 18 is attached to the reservoir 14.

The pump device 10 is coupled to an infusion device, such as a syringe needle and/or a cannula, as described below, so that the medicament is infused into the user. Infusion methods are known in the art.

The reservoir 14 is operated, in accordance with instructions received from a pump controller unit 19. The reservoir 14 includes as least one stationary arm and at least one rotating arm, such that on receiving appropriate instructions from the controller, the drive mechanism 26 rotates the reservoir 14, such that a rotatable arm attached to an inner wall of the reservoir rotates relative to the stationary arm and at least one predetermined dosage of the at least one medicament 16 is impelled into the medicament outlet conduit 18, as described below. Thus, a predetermined dosage of the medicament is infused into the user, in accordance with medical requirements.

The medical infusion instructions, such as quantity of medicament, number of medicaments for infusion, times of infusion and infusion rates, are supplied by the user and/or medical staff instructions, typically, to a remote controller 21. The remote controller 21 forwards the instructions, wirelessly, such as by EM signals or acoustic signals, and/or by wire to the pump controller 19. The pump controller 19 operates the drive mechanism 26, in accordance with the received instructions.

FIG. 1 shows the remote controller 21 is remotely located. Alternatively, the pump 10 includes a self-controlled functionality and does not require an external remote controller panel 21

Figure 2:
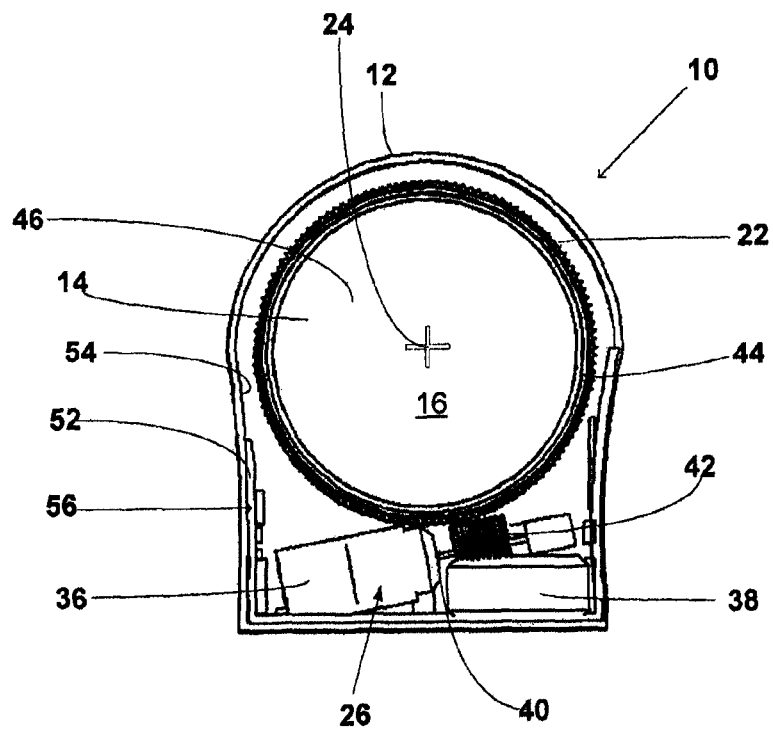
FIG. 2 shows further details of the fluid infusion pump device shown in FIG. 1, in accordance with a preferred embodiment of the present invention.
Figure 8:
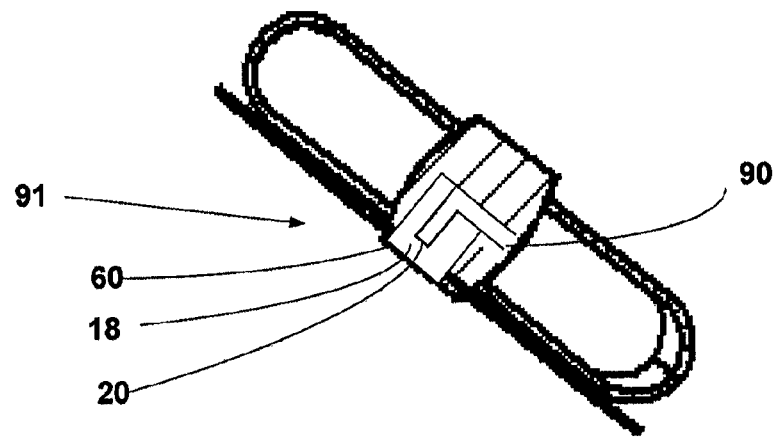
FIG. 8 shows the fluid flow system in the center axle, in accordance with a preferred embodiment of the present invention.

Reference is now made to FIG. 2, which shows further details of the fluid infusion pump device 10 for infusing at least one fluid-medicament to the user, in accordance with a preferred embodiment of the present invention. The medicament outlet conduit 18 is coupled to the reservoir 14 for infusing the medicament 16 into the user. An infusion needle 20 is fluidly coupled to the medicament outlet 18 conduit and the infusion needle 20 is stored within a central axle 60 (FIG. 8). A controlled supply of the medicament 16 is thus applied to the user by the pump device 10.

The reservoir 14 is attached to a pump chassis 22 and is rotated about a central axis 24 of the housing 12 by means of a drive mechanism 26. The housing 12 includes, inter alia, an upper pin 28 and a lower pin 30 (FIG. 6), which are inserted and locked into corresponding indents 32 and 34 (FIG. 5), respectively, in the reservoir 14, as is known in the art. During operation of the pump device 10, the reservoir 14 rotates about the central axis 24.

The drive mechanism 26 rotates the medicament reservoir 14, as described below, about the central axis 24 of the housing 12, thereby impelling at least one predetermined dosage of the at least one fluid-medicament 16 out of the reservoir 14 and into the user, via the medicament outlet conduit 18.

Figure 3:
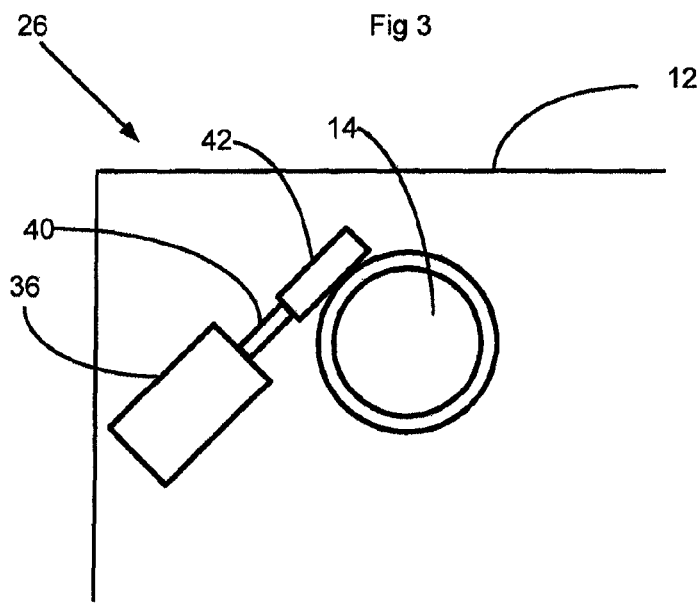
FIG. 3 shows the drive mechanism of the pump device, in accordance with a preferred embodiment of the present invention.

Reference is now also made to FIG. 3, which shows the drive mechanism 26, in accordance with a preferred embodiment of the present invention. The drive mechanism 26, typically, includes, inter alia, a motor 36, such as an electric DC stepper motor, an AC motor, a piezoelectric motor, a motor including a shape memory element SME, such as nitinol wire, which is typically powered by a power supply 38 (FIG. 2), such as at least one battery. The motor 36 is typically mechanically coupled to the reservoir 14 by means of a drive shaft 40 and a worm gear device 42, including a worm wheel 44, which is attached to the chassis 22 (FIG. 2). Alternatively, a teeth wheel gear mechanism is used to rotate the reservoir 14.

The drive mechanism 26 includes a mechanical drive mechanism and/or an electromechanical drive mechanism.

Alternatively, the drive mechanism 26 is attached to the central axle 60 (FIG. 5) thereby rotating the central axle 60 and the reservoir 14 is stationary.

Additionally or alternatively, the power supply is located externally to the pump device 10 and supplies power to the motor 36, as is known in the art.

Figure 4:
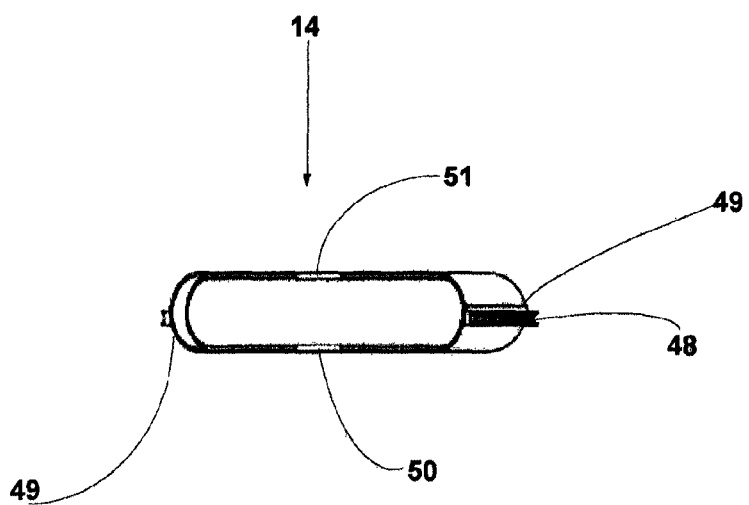
FIG. 4 presents an alternative arrangement of the mechanical coupling of the reservoir to the drive mechanism, in accordance with another preferred embodiment of the present invention.

Reference is now made to FIG. 4, which presents an alternative arrangement of the mechanical coupling of the reservoir 14 to the drive mechanism 24, in accordance with another preferred embodiment of the present invention. In the mechanical coupling shown in FIG. 4, a worm wheel 48 is directly attached to a contoured outer wall 49 of the reservoir 14 and the reservoir 14 is directly rotated by the drive mechanism 26. This arrangement precludes attaching the worm wheel 48 to the chassis 26.

Figure 5:
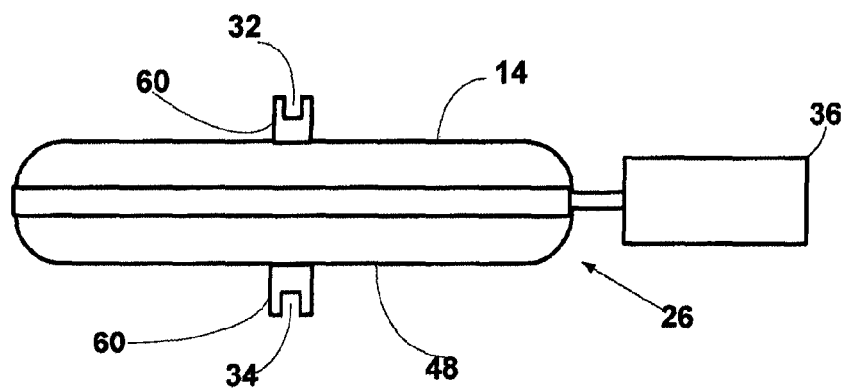
FIG. 5 presents a view of the reservoir as coupled to the drive mechanism, in accordance with a preferred embodiment of the present invention.

FIG. 4 also shows a lower cutout 50 and an upper cutout 51 for receiving the central axle 60 (FIG. 5).

Figure 6:
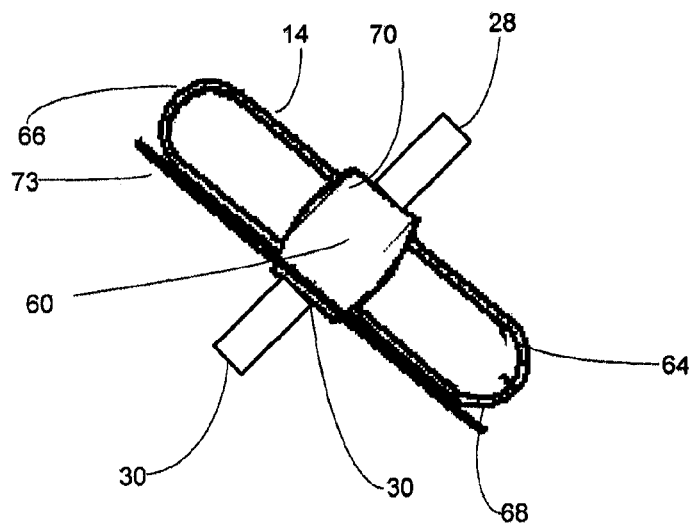
FIG. 6 presents a side-view of the reservoir, in accordance with a preferred embodiment of the present invention.

It is also show in FIG. 4 that the contoured outer wall 49 of the reservoir 14 preferably has an ellipsoidal geometry. The ellipsoidal contour of the reservoir 14 provides an optimal ratio between the fluid volume contained in the reservoir 14 to an outer surface area of the reservoir 14. The central axle 60 of the reservoir 14 also has ellipsoidal cross-section (FIG. 6).

The reservoir 14 and/or the central axis 60 may also have alternative geometrical cross-sections, such as a spherical geometry. It is appreciated that for the alternative cross-sections, the various elements of the reservoir require appropriate modification.

A PCB 52 (FIG. 2) is typically attached to an inner surface 54 of the housing 12 and includes a control unit 56 for controlling the operation of the pump 10, such that the rotation of the reservoir 14 and infusion of the medicament 16 is controlled such that a required and predetermined quantity of the medicament 16 is provided by the pump device 10 to the user. Typically, the control unit 56 also controls communications with the remote controller 21, an infusion-quantity of the medicament 16, a time of infusion of the medicament 16 into the user and a flow rate infusion of the at least one medicament 16 into the user.

It is appreciated that the pump device 10 is also applicable for situations which require accurate quantities of fluid to be administered in non-medical situations, as described below.

Reference is now made to FIG. 5, which presents a view of the reservoir 14 as coupled to the drive mechanism 26, in accordance with a preferred embodiment of the present invention. The reservoir 14 includes, inter alia, a contoured central axle 60 of rotation, the upper pin 28 (FIG. 6) is inserted into the upper insert 32 and the lower pin 30 (FIG. 6) is inserted into the lower inset lower insert 34.

Reference is now made to FIG. 6, which presents a cross-sectional view 62 of the reservoir 14, in accordance with a preferred embodiment of the present invention. The reservoir 14 includes, inter alia, a central axis 60 and the upper pin 28 and the lower pin 30 are inserted into the center axle 60 of the reservoir 14. The upper pin 28 and the lower pin 30 are inserted and locked in the corresponding indents 32 and 34 of the central axle 60. Typically, the drive mechanism 26 rotates the reservoir 14 relative to the central axis 60.

It is seen that the reservoir 14 typically has an ellipsoidal contour outer surface 68. The contoured surface 68 provides structural strength and stiffness to the reservoir 14.

Alternatively, the drive mechanism 26 is mechanically coupled to the central axle 60 and the central axle 60 is rotated and the reservoir 14 is stationary.

It is seen in FIG. 6 that an encoder 73 is attached to the reservoir 14. The encoder 73 determines the rotation of the reservoir 14 thereby ensuring that the required quantity of the medicament 16 is infused into the user, as described below.

Figure 7A:
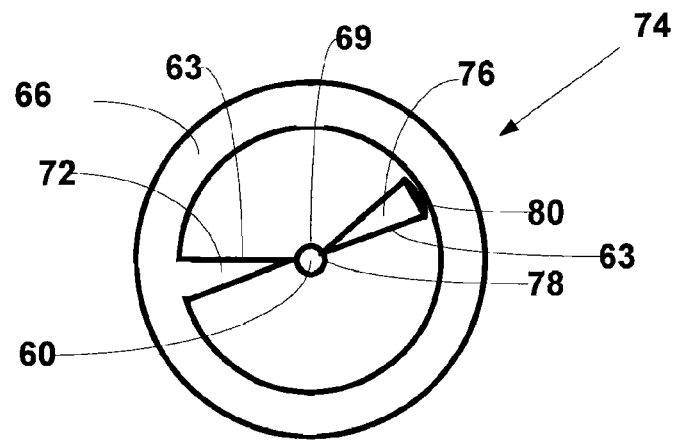
FIGS. 7A, 7B and 7C show an internal structure of the reservoir, in accordance with a preferred embodiment of the present invention.
Figure 7B:
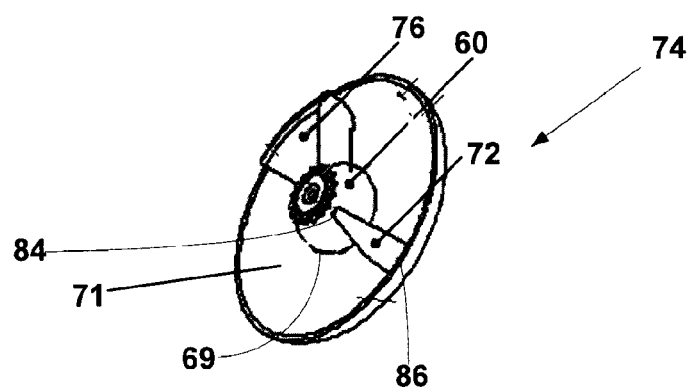
Figure 7C:
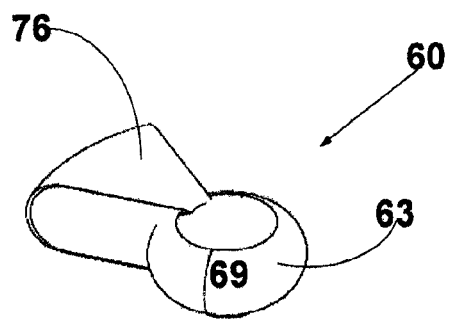

Reference is now made to FIGS. 7A, 7B and 7C, which show an internal structure 74 of the reservoir 14, in accordance with a preferred embodiment of the present invention. It is shown in FIG. 7A that the reservoir 14 also includes, inter alia, a peripheral wall 66, at least one rotating arm 72 and at least one stationary arm 76. The stationary arm 76 has a proximal end 78 and a contoured distal end 80. The proximal end 78 is attached to a contoured surface 69 of the central axle 60 and the contoured proximal end 80 abuts the peripheral wall 66.

It is appreciated that the contoured end 80 has a corresponding contour to the outer surface 49 of the reservoir 14.

Reference is now made to FIG. 7B, which shows that the rotating arm 72 also includes a contoured proximal end 84 and a contoured distal end 86. The contoured proximal end 84 is attached to the contoured surface 69 of the center axle 60 and the contoured distal end 86 is attached to the peripheral wall 66 of the reservoir 14. Thus, on rotation of the reservoir 14, the rotating arm 72 rotates with the reservoir 14, about the center axle 60 and the medicament is impelled out of the reservoir 14 into the outlet 18. It is appreciated that the at least one rotating arm 72 rotates relative to the at least one stationary arm 76.

It is appreciated that the contoured ends 84 and 86 have contours which correspond to the contour of the outer surface 49 of the reservoir 14 and the contour 69 of the central axle 60, respectively.

In order to prevent leakage of the fluid 16 from the reservoir 14, the peripheral wall 66, the contoured surface 69 of the center axle 60, the peripheries of the stationary and the rotating arms are coated with a sealant 63, such as rubber, Silicone rubber, polymerized siloxanes and/or polysiloxanes, such as WKT and Polydimethylsiloxane.

It is appreciated that in addition to the use of the sealant 63 for preventing leakage, the peripheral wall 49, the peripheries of the stationary and the rotating arms have corresponding smooth and contoured walls without sharp edges and corners.

FIG. 7C shows the contoured center axle 60 coated with the sealant 63. The smooth contoured wall of the central axle 60 coated with the sealant 63, prevent seepage and leakage of fluid between the various compartments and chambers of the pump device 10.

The sealant 63 prevents seepage and leakage of the fluid medicament 16 from the full compartments of the reservoir 14 to partially and/or empty portions of the reservoir 14, as the reservoir 14 rotates. In addition, the sealant 63 prevents leakage and seepage of replacement air (as described below) from the fluid-free portions of the compartments to fluid-filled compartments of the reservoir 14.

Reference is now made to FIG. 8, which shows a fluid flow system 91 in the center axle 60, in accordance with a preferred embodiment of the present invention. The fluid flow system 91 includes at least one outlet fluid channel 90. The channel 90 is located within the medicament outlet conduit 18 and is coupled to the infusion needle 20. The fusion needle 20 is stored within the central axle 60. For infusion, a septum in the cannula is inserted into the outlet 18, such that the needle 20 pierces the septum, as is known in the art.

The fluid channel 90 is located within the stationary arm 76. The rotation of the reservoir 14 impels the predetermined dosage of the medicament 16 to the medicament outlet 18 via the channel 90 and into the user.

Alternatively, the fluid channel 90 is located within the rotating arm 72. The rotation of the reservoir 14 impels the predetermined dosage of the medicament 16 to the medicament outlet 18 via the fluid channel 90.

Additionally or alternatively, each one of the at least one rotating arm 72 and each one of the at least the stationary arm 76 includes at least one outlet fluid channel fluidly coupled to the medicament outlet conduit 18, as described below. On rotation of the reservoir 14, the predetermined dosage of the medicament 16 is impelled through the respective outlet fluid channels located within the rotating arm 72 and stationary arm 76, impelling the fluid 16 through the medicament outlet 18.

Figure 9:
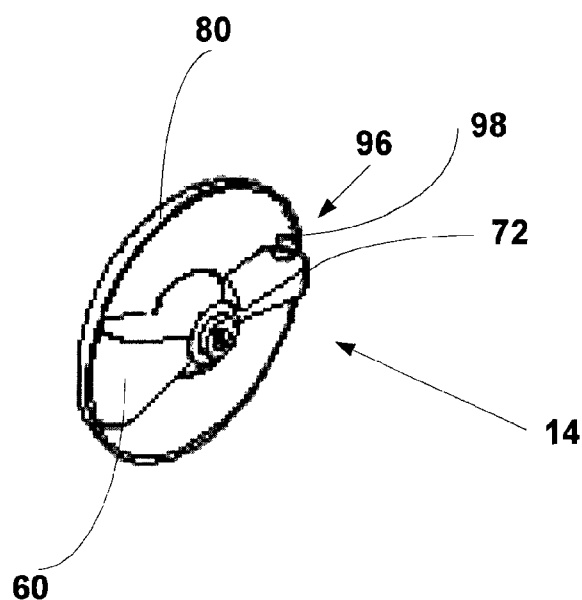
FIG. 9 presents a top-view of the base of the infusion pump device, in accordance with a preferred embodiment of the present invention.

Reference is now made to FIG. 9, which presents a view of the reservoir 14, in accordance with a preferred embodiment of the invention. In FIG. 9 it is shown that as the rotating arm 72 rotates about the central axle 60, replacement air 96 flows into the reservoir 14 via an air inlet port 98. Replacement air 96 flows into the reservoir 14 and replaces the quantity of at least one fluid-medicament ejected from the pump device 10.

Figure 10A:
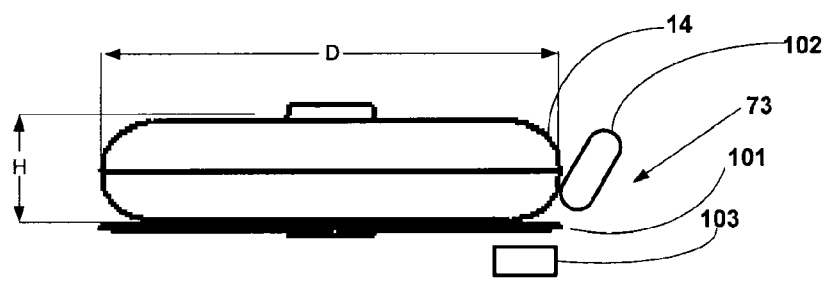
FIG. 10A shows the encoder unit, in accordance with a preferred embodiment of the present invention.

Reference is now also made to FIG. 10A, which shows the encoder 73, includes, inter alia, an inscribed disc 101, a radiation source 102 and a reading head 103, such as an optical reading head, a magnetic reading head, an induction reading head and/or any combination thereof. Graduation marks 104 are included on the disc 101 (FIG. 10B), such that as the disc 101 rotates, the encoder 73 determines a rotation of the reservoir 14. The encoder 73 is wirelessly and/or wirely connected to the control unit 56 (FIG. 2).

In FIG. 10A, the central axle 60 rotates and the reservoir is stationary.

Figure 10B:
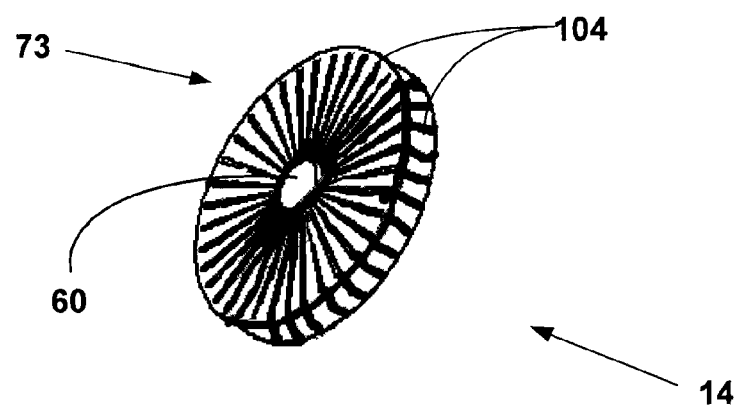
FIG. 10B shows an encoder disc and graduation marks, in accordance with a preferred embodiment of the present invention.

Reference is now made to FIG. 10B which shows the graduation marks 104, in accordance with a preferred embodiment of the present invention. In FIG. 10B the central axle 60 is stationary and the reservoir 14 rotates.

As the reservoir 14 rotates, the graduation marks 104 pass the reading head 103 and the reading head 103 records the number of marks sensed, as known in the art. The encoder 73 processes the data and determines the quantity of medicament being released from the reservoir 14 and impelled into the medicament outlet conduit 18. The encoder 73 records the operational time interval of the reservoir 14 and the control unit 56 determines a flow rate of the fluid 16 infused in the user. The control unit 56 also determines if a required quantity of the medicament has been infused into the user.

Furthermore, the control unit 56 determines if the quantity of ejected fluid fulfills the medical requirements. If the medical requirements are fulfilled, the control 56 instructs the drive mechanism 26 to suspend further rotation of the reservoir 14.

As describe below (FIGS. 26A and 26B), the user of the device 10 selects an infusion application 94 on the remote panel 21 (FIG. 1) for the infusion of the medicament 16 in accordance to the user's medical requirements, as described below, and selects a predetermined dosage of the medicament 16, in accordance with the user's requirements. The drive mechanism 26 rotates the reservoir 14 accordingly. The rotating arm 72 impels the predetermined dosage of the fluid-medicament 16 through the outlet fluid port 90 and into the outlet medicament channel 92. The predetermined dosage of the medicament 16 flows through the medicament outlet conduit 18 and into the syringe needle 20.

Since medicament infusion into a patient requires the infusion of accurate quantities of the medicament and as typically mechanical devices have an inherent inaccuracy, the encoder 73 permits a closed-loop control for the reservoir angular rotation thereby reducing mechanical inaccuracies in determining the rotation of the reservoir. In the present invention, the accuracy of rotation is determined by the accuracy of the location of the graduation marks 104. Thus, the pump device 10 provides a cost efficient and accurate pump device for administering required and accurate quantities of medicaments to the patient.

Figure 11:
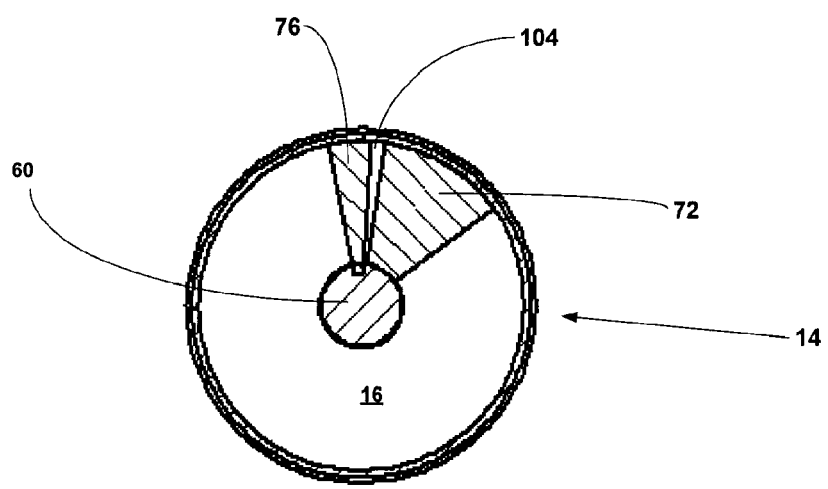
FIG. 11 shows the initial locations of the rotating arm and the stationary arm, prior to infusion of the medicament, in accordance with a preferred embodiment of the present invention.

Reference is now made to FIG. 11, which presents a view of the reservoir 14 filled with the medicament 16 and the initial locations of the rotating arm 72 and the stationary arm 76, prior to infusion of the medicament 16 into the user. It is shown in FIG. 11 that the stationary arm 76 and the rotating arm 72 are initially not in contact. There is an air gap 104 between the arms 76 and 72.

Reference is now made to FIG. 12, which shows a location of the rotating arm 72 for a typical situation in which the reservoir 14 is partially empty, in accordance with a preferred embodiment of the present invention. It is shown in FIG. 12 that as the rotating arm 72 rotates replacement air 108 flows into the reservoir 14, through the air gap 96 and replaces the fluid 16 which has been pumped out of the device 10.

Reference is now made to FIG. 13, which shows an end-of-travel location of the rotating arm 72 for a typical situation in which the reservoir 14 is empty, in accordance with a preferred embodiment of the present invention. It is shown in FIG. 13 that the rotating arm 72 has reached the end of its travel and the replacement air 108 fills the reservoir 14.

Reference is now made to FIG. 14, which presents a view of a reservoir 109 in which a stationary arm 110 extends diametrically through a central axle 111 and partitions the reservoir 14 into at least two compartments 112 and 114, in accordance with another preferred embodiment of the present invention. The reservoir 109 includes a rotating arm 116 which extends diametrically through the central axle 111 as well as two initial air gaps 118 and 120. As reservoir 109 rotates replacement air 108 flows into the reservoir 109, as described above, and replaces the fluid which has been pumped out of the device 10.

It is appreciated that the compartments 112 and 114 can store different medicaments 122 and 124, such as morphine and/or ziconotide.

On activation of the device 109, the arm 116 rotates in a clockwise direction, as indicated by an arrow 126 and the reservoir 109 releases the medicaments 122 and 124 into the medicament outlet 18.

It is further appreciated that the compartments 122 and 124 are not necessarily of the same volumetric size and thus each compartment is able to store different capacities of medicaments 122 and 124.

It is additionally appreciated that due to the reservoir 109 including the diametrically positioned arms 110 and 116, the reservoir 109 is able to more accurately administer quantities of medicaments 122 and 124 in comparison to the reservoir 14, described with respect to FIGS. 11-13. In the reservoir 109, the central axle 111 jitter during rotation of the reservoir 109 is limited, since the axle 111 is fixed to the base 68 by means of the diametrical stationary arm 110.

Reference is now made to FIG. 15, which shows a location of the rotating arm 116 for a typical situation in which the reservoir 109 is partially empty, in accordance with another preferred embodiment of the present invention. It is shown in FIG. 15 that as the rotating arm 116 rotates replacement air 128 flows into the reservoir 109 and replaces the medicaments 122 and 124 which have been pumped out of the pump 10.

Reference is now made to FIG. 16, which shows a location of the rotating arm 116 for a typical situation in which the reservoir 109 is empty, in accordance with another preferred embodiment of the present invention. It is shown in FIG. 16 that the rotating arm 116 has reached the end of its travel and the replacement air 128 fills the compartments 122 and 124.

Figure 17A:
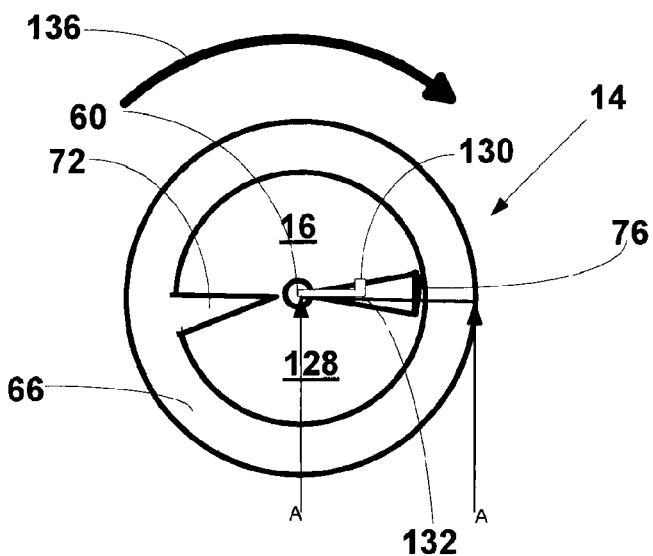
FIGS. 17A and 17B present a top-view and a side-view, respectively, of a reservoir in which the medicament exits the reservoir via the rotating arm, in accordance with a preferred embodiment of the present invention.

Reference is now made to FIG. 17A which presents a top view of the reservoir 14, in accordance with a preferred embodiment of the present invention.

Figure 17B:
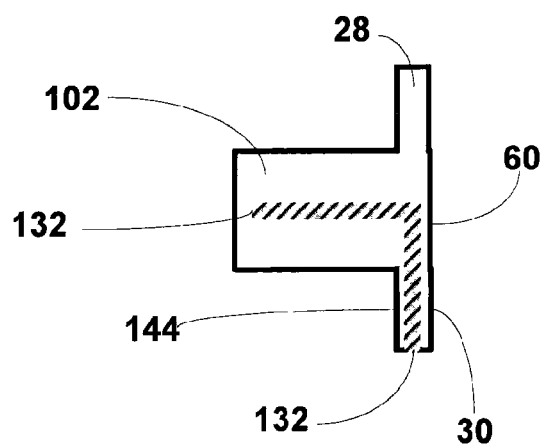

Reference is also made to FIG. 17B which presents a side view of the reservoir 14 in a direction A-A of FIG. 17A, in accordance with a preferred embodiment of the present invention.

FIGS. 17A and 17B show a fluid outlet port 130 is located in the stationary arm 76 and is fluidly coupled to a fluid flow channel 132 located within the arm 76. The fluid flow channel is fluidly coupled to the fluid channel 132, which is coupled to the medicament outlet 18 (not shown). In FIG. 17B it is shown that the fluid channel 132 extends into the lower pin 30, such that the medicament 16 exits the reservoir via the lower pin 30. Alternatively, the fluid channel 132 extends into the upper pin 28, positioned such that the medicament exits the reservoir 14 via the upper pin 28.

Additionally or alternatively, the fluid channel 132 is bifurcated and extends into the lower pin 30 and the upper pin 28, such that the medicament flows from the reservoir 14 via the lower 30 and upper pin 28.

As reservoir 14 rotates replacement air flows into the reservoir 14, as described above, and replaces the fluid which has been pumped out of the device 10.

FIG. 17A shows that the reservoir 14 is partially empty and as the rotating arm 72 rotates in a clockwise direction, as indicated by a direction arrow 136, the medicament 16 flows through the port 130, located in the stationary arm 76.

Figure 18A:
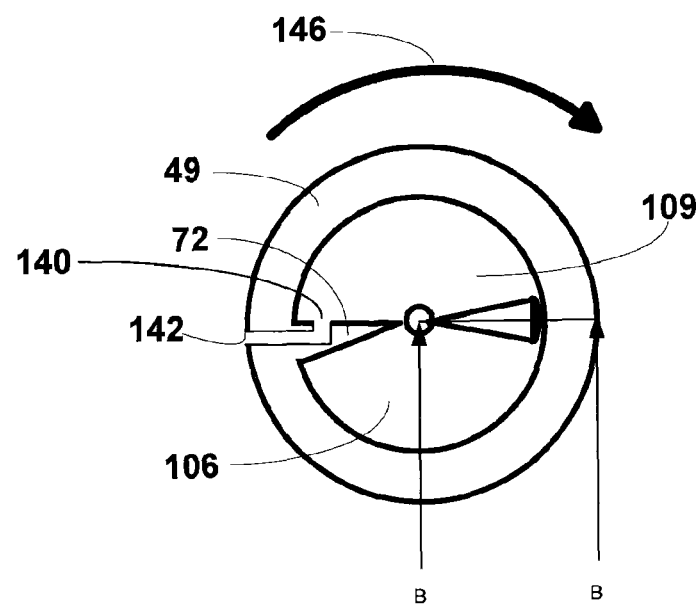
FIGS. 18A and 18B present a top-view and a side-view, respectively, of the full reservoir in which the medicament exits the reservoir via the stationary arm, in accordance with a preferred embodiment of the present invention.

Reference is now made to FIG. 18A which presents a view of the reservoir 14, in accordance with an alternative preferred embodiment of the present invention.

Figure 18B:
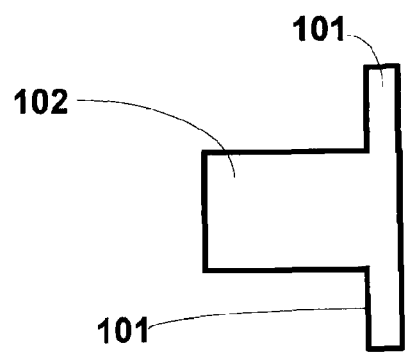

Reference is also made to FIG. 18B which presents a side view of the reservoir 14 in a direction B-B of FIG. 18A, in accordance with an alternative preferred embodiment of the present invention.

FIGS. 18A and 18B show a fluid outlet port 140 is located in the rotating arm 72 and is fluidly coupled to a fluid flow channel 142 located within the arm 72 and outer wall 49 of the reservoir 14. The fluid flow channel 142 is fluidly coupled to the medicament outlet 18 (not shown). In FIG. 18A, an alternative embodiment of the present invention is shown in which the channel 142 extends through the outer 49 and the fluid 16 flows to the outlet 18 via the wall 49 and not through the central axle 60.

FIG. 18A shows that the reservoir 14 is partially empty and as the rotating arm 72 rotates in a clockwise direction, as indicated by a direction arrow 146, the medicament 16 flows through the port 140, located in the rotating arm 72.

Additionally or alternatively, the channel 142 is bifurcated and extends into the central axle 60 and the wall 49, such that the medicament 16 flows out of the reservoir 14 via the axle 60 and the wall 49.

As reservoir 14 rotates replacement air flows into the reservoir 14, as described above, and replaces the fluid which has been pumped out of the device 10.

Figure 19A:
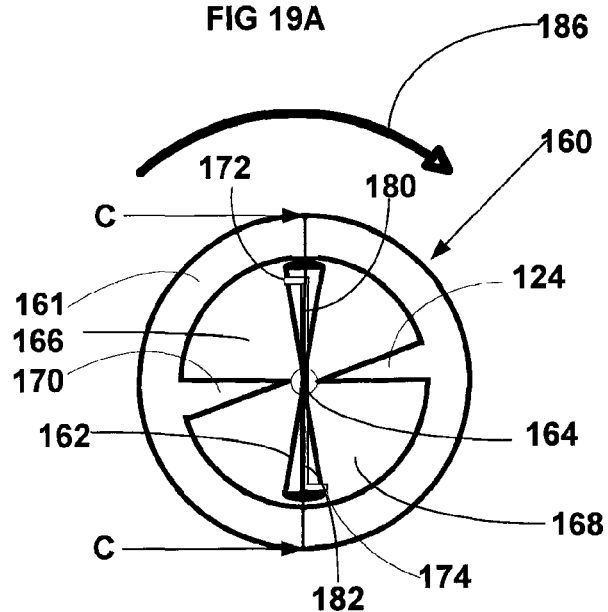
FIGS. 19A and 19B present a top-view and a side-view, respectively, of a two-compartment reservoir in which the medicament exits the reservoir via the stationary arm, in accordance with yet another preferred embodiment of the present invention.

Reference is now made to FIG. 19A which presents a top-view of a reservoir 160, in accordance with yet another preferred embodiment of the present invention.

Figure 19B:
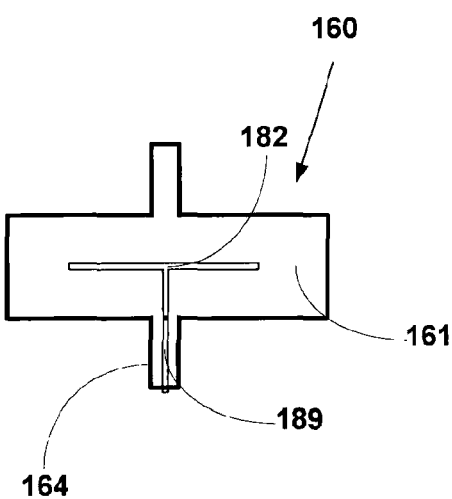

Reference is also made to FIG. 19B which presents a side view of the reservoir 160 in a direction C-C of FIG. 19A, in accordance with yet another preferred embodiment of the present invention.

FIGS. 19A and 19B present a cross-sectional view and a side-view, respectively, of the reservoir 160, including an outer wall 161 and a stationary arm 162 which extends diametrically through a central axle 164 and partitions the reservoir 160 into at least two compartments 166 and 168. The reservoir 160 includes a rotating arm 170 which also extends diametrically through the central axle 164.

It is shown in FIG. 19A that the stationary arm 162 includes at least two fluid outlet ports 172 and 174. The ports 172 and 174 are fluidly coupled to fluid flow channels 180 and 182, respectively. The fluid flow channels 180 and 182 are fluidly coupled to the medicament outlet 18 (FIG. 19B).

FIG. 19A shows that the reservoir 160 is partially full and as the rotating arm rotates in a clockwise direction, as indicated by a direction arrow 186, the medicament 16 flows through the ports 172 and 174, located in the stationary arm 162.

Additionally or alternatively, the channels 180 and 182 are fluidly coupled to a channel 189 which extends into the central axle 164 and the wall 161, such that the medicament 16 flows out of the reservoir 160 via the axle 164 and the wall 161.

As reservoir 160 rotates replacement air flows into the reservoir 160, as described above, and replaces the fluid which has been pumped out of the device 10.

Figure 20A:
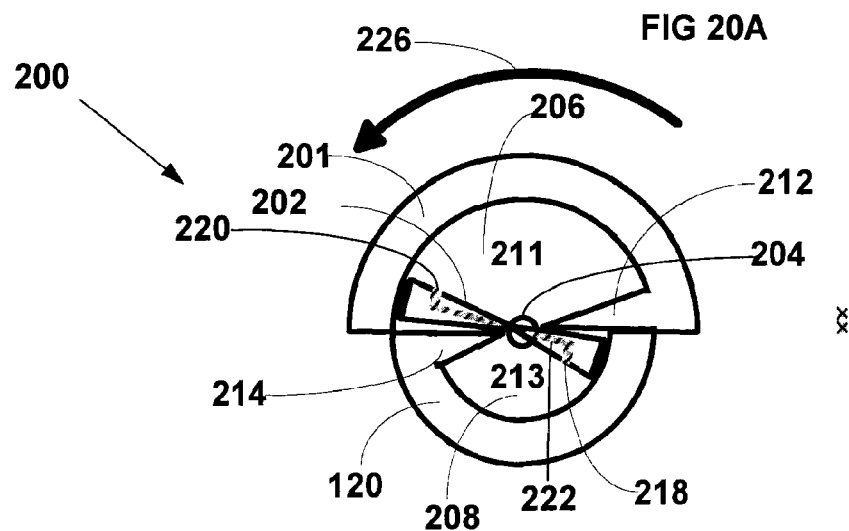
FIGS. 20A and 20B present a cross-sectional view and a side-view, respectively, of a two-compartment reservoir with equal fluid capacities, in accordance with yet a further preferred embodiment of the present invention.

Reference is now made to FIG. 20A, which presents a view of a reservoir 200, in accordance with yet a further preferred embodiment of the present invention.

Figure 20B:
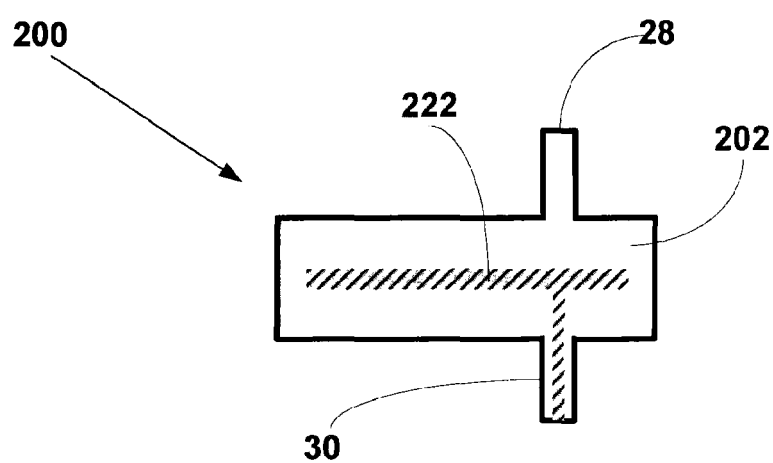

Reference is also made to FIG. 20B which presents a side-view of the reservoir 200 in a direction D-D of FIG. 20A, in accordance with yet a further preferred embodiment of the present invention.

FIGS. 20A and 20B present a top-view and a side-view, respectively, of the reservoir 200, including an outer wall 201 and a stationary arm 202 which extends through a central axle 204 and partitions the reservoir 200 into at least two compartments 206 and 208, of unequal fluid capacities. Typically, the compartment 206 has a larger capacity than the compartment 208. The reservoir 200 includes rotating arm 212 and 214 which extend towards the central axle 204. The arm 212 is typically longer than the arm 214. The arm 212 rotates in the larger compartment 206 and the arm 214 rotates in the smaller compartment 208.

It is shown in FIG. 20A that the stationary arm 202 includes at least two fluid outlet ports 218 and 220. The ports 218 and 220 are fluidly coupled to a fluid flow channel 222

FIG. 20A shows that the reservoir 200 is full and as the rotating arms 212 and 214 rotate in an anti-clockwise direction, as indicated by a direction arrow 226, the medicament 16 flows through the ports 218 and 220, located in the stationary arm 202.

It is appreciated that the reservoir 200 provides unequal capacities of medicaments to the user. Typically, the compartment 206 includes a larger capacity of a medicament 211 than the compartment 208 provides of the medicament 213.

Thus, the user is able to receive unequal capacities of medicaments 211 and 213.

As reservoir 200 rotates replacement air flows into the reservoir 200, as described above, and replaces the fluid which has been pumped out of the device 10.

Figure 21:
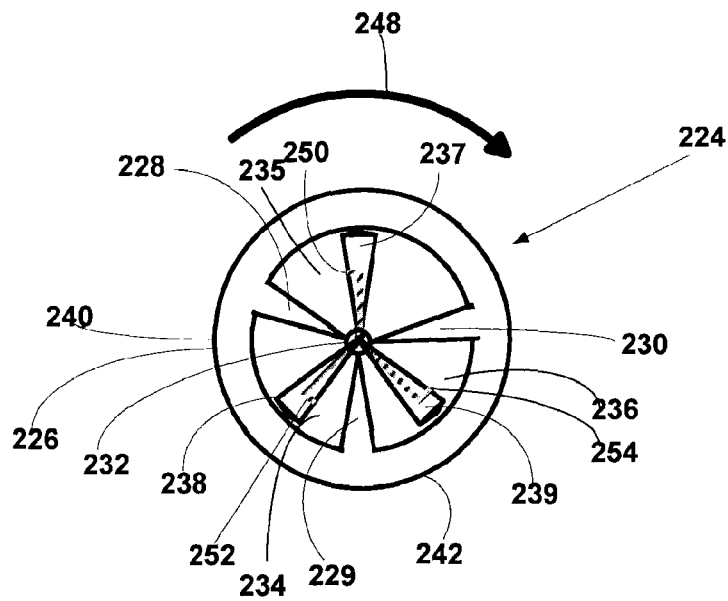
FIG. 21 presents a cross-sectional view and a side-view, respectively, of a two-compartment reservoir with unequal fluid capacities, in accordance with yet a further preferred embodiment of the present invention.

Reference is now made to FIG. 21, which presents a cross-sectional view of a reservoir 224, in accordance with yet another preferred embodiment of the present invention.

FIG. 21 presents a top-view of the reservoir 224, including an outer wall 226 and at least three stationary arms 237, 238 and 239 which are attached to a central axle 232 and partition the reservoir 224 into at least three compartments 234, 235 and 236, respectively. The reservoir 224 includes at least three corresponding rotating arms 228, 229 and 230 which are attached to a wall 226 of the reservoir 224.

FIG. 21 shows that the rotating arms 228, 229 and 230 rotate in a clockwise direction, as indicated by a direction arrow 248.

It is shown in FIG. 21 that stationary arms 237, 238 and 239 include at least three fluid outlet ports 250, 252 and 254, respectively. The ports 250, 252 and 254 are fluidly coupled to corresponding flow channels (not shown). The fluid flow channels are fluidly coupled to the medicament outlet 18 (FIG. 1).

FIG. 21 shows that the reservoir 224 is able to provide the user with at least three different medicaments.

It is appreciated that the reservoir 224 can include any number of compartments.

Figure 22:
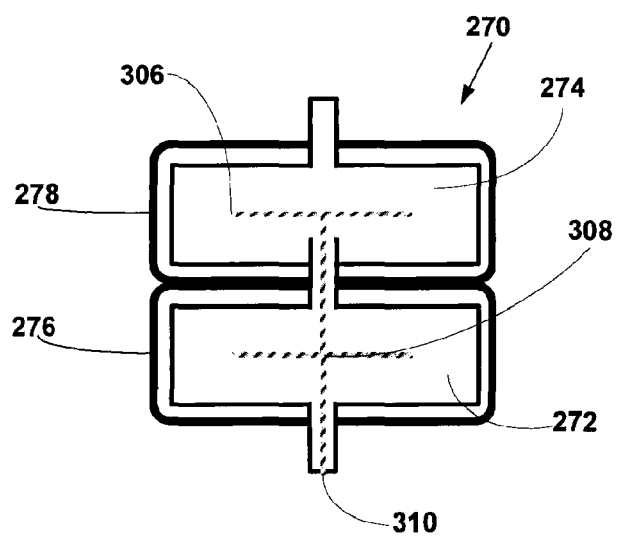
FIG. 22 presents a side-view of a stacked reservoir with at least two compartments having equal fluid capacities; in accordance with another preferred embodiment of the present invention.

Reference is now made to FIG. 22 which presents a side-view of a stacked reservoir 270, in accordance with yet another preferred embodiment of the present invention. The stacked reservoir 270 includes, inter alia, at least two reservoirs, a lower reservoir 272 and an upper reservoir 274, contained with a lower housing 276 and an upper housing 278, respectively. Typically, the lower housing 272 and the upper housing 274 are mechanically coupled and the lower and upper reservoirs 272 and 274 are of equal fluid capacities.

The upper reservoir 274 includes a fluid exit channel 306 and the lower reservoir 272 includes a fluid exit channel 308. The medicament exits the upper reservoir 274 through the channel 306 and the medicament in the lower reservoir 272 exits via the channel 308. The medicament then flows through a fluid channel 310 towards the medicament outlet 18 (not shown).

Reference is now made to FIG. 23 which presents a side-view of a stacked reservoir 320, in accordance with yet a further preferred embodiment of the present invention. The stacked reservoir 320 includes, inter alia, at least two reservoirs, a lower reservoir 322 and an upper reservoir 324, contained with a lower housing 326 and an upper housing 328, respectively. Typically, the lower housing 326 and the upper housing 328 are mechanically coupled and the lower and upper reservoirs 322 and 324 are of unequal fluid capacities.

The upper reservoir 324 includes a fluid exit channel 330 and the lower reservoir 322 includes a fluid exit channel 332. The medicament exits the upper reservoir 324 through the channel 330 and the medicament in the lower reservoir 322 exits via a channel 334. The medicament then flows through a fluid channel 332 towards the medicament outlet 18 (not shown).

It is appreciated that the reservoir 320 provides unequal capacities of medicaments to the user.

Reference is now made to FIGS. 24A, 24B and 24C, which show reservoirs having different wall geometries, in accordance with yet a further preferred embodiment of the invention.

FIG. 24A shows a reservoir 400 with a geometrical shape shown in the figure. The reservoir 400 includes, inter alia, a reservoir wall 402, a rotating arm 404, a stationary arm 406, a fluid channel 408 and a replacement air inlet port 409.

FIG. 24B shows a reservoir 410 with a geometrical shape shown in the figure. The reservoir 410 includes, inter alia, a reservoir wall 412, a rotating arm 414, a stationary arm 416, a fluid channel 418 and a replacement air inlet port 419

FIG. 24C shows a reservoir 420 with a geometrical shape shown in the figure. The reservoir 420 includes, inter alia, a reservoir wall 422, a rotating arm 424, a stationary arm 426, a fluid channel 428 and a replacement air inlet port 429.

Figure 25:
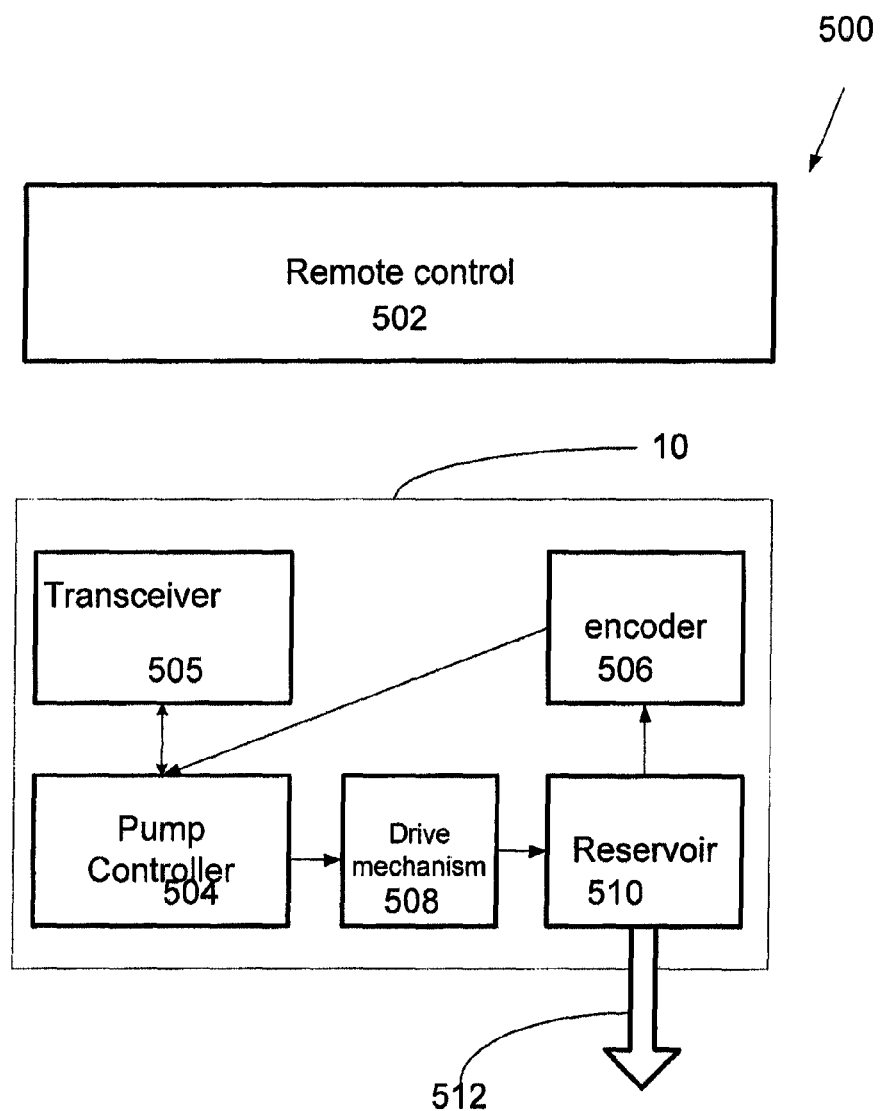
FIG. 25 presents a control system for controlling the operation of the pump device, in accordance with a preferred embodiment of the present invention.

Reference is now made to FIG. 25 which shows a control system 500 for controlling the operation of the pump device 10, in accordance with a preferred embodiment of the present invention. A user inputs the infusion data into a remote control device 502, including, for example, the quantity of infusion-medicament and the time for the infusion, in accordance with medical requirements. The user activates the remote control device 502 which transmits to a transceiver 505 located in the device 10. The transceiver 505 forwards the requisite flow data to a controller 504. The controller 504 instructs a drive mechanism 508 to operate a fluid reservoir 510, which impels the fluid to a medicament outlet 512.

In addition, the controller 504 and the encoder 506 measure and determine the quantity of medicament remaining in the reservoir 510 and communicate this information to the remote control 502 via the transceiver 505.

Figure 26A:
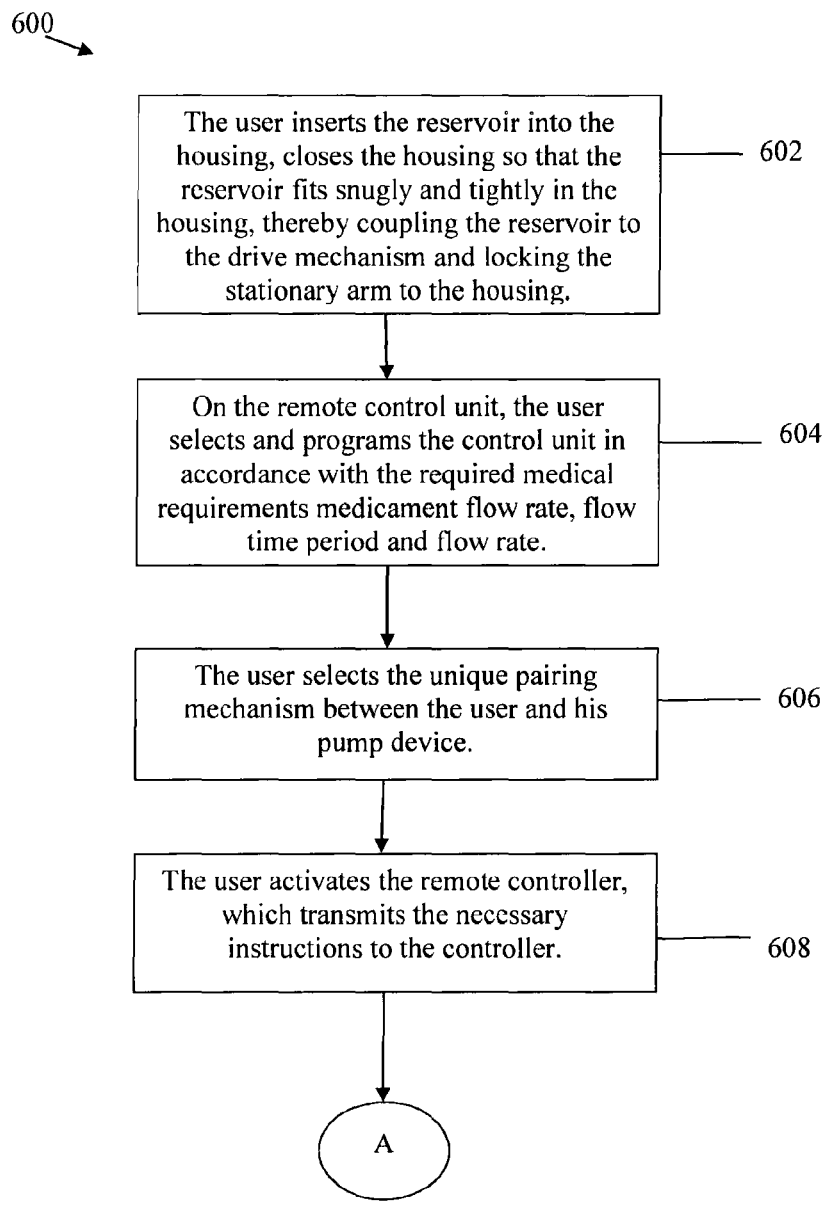
FIGS. 26A and 26B, combined, present a flow chart for the process of infusing a fluid-medicament into the user, in accordance with a preferred embodiment of the invention.
Figure 26B:
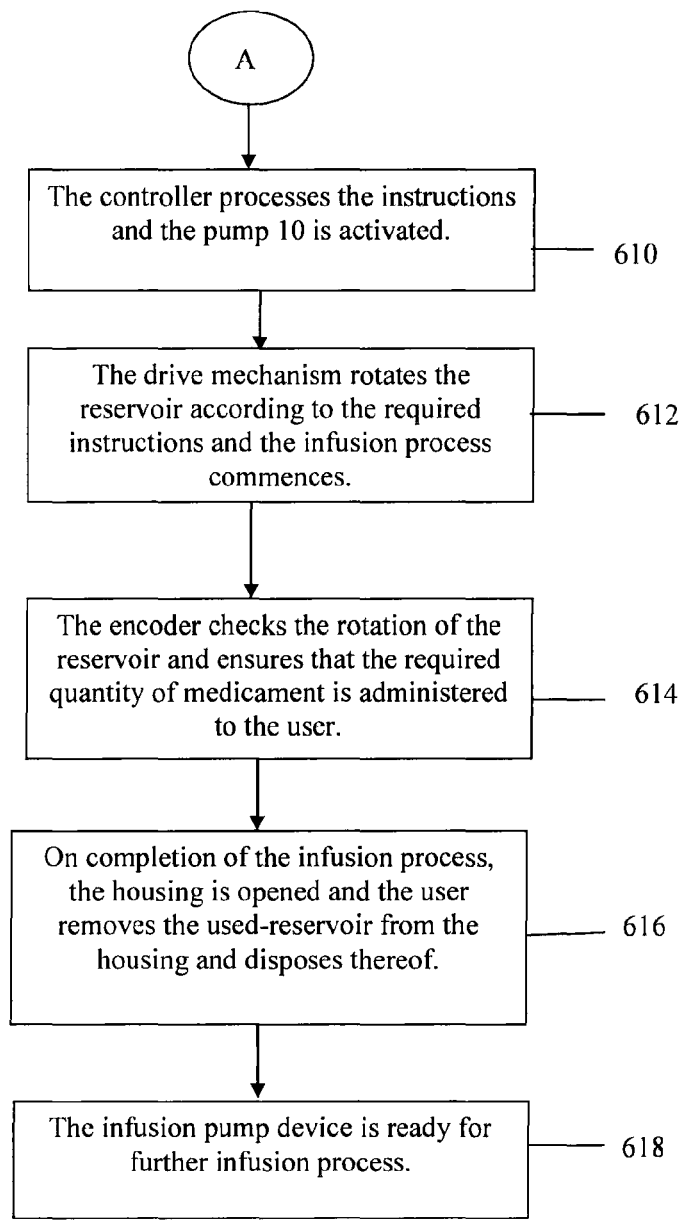

Reference is now made to FIGS. 26A and 26B, which present a flow chart 600 for the infusion of a medicament fluid 16 into the user.

In step 602, the user inserts the reservoir into the housing, closes the housing so that the reservoir fits snugly and tightly in the housing, thereby coupling the reservoir to the drive mechanism and locking the stationary arm to the housing.

In step 604, on the remote control unit, the user selects and programs the control unit in accordance with the required medical requirements medicament flow rate, flow time period and flow rate.

In step 606, the user selects the unique pairing mechanism between the user and his pump device thereby ensuring that the user communicates with a single pump, only and does not interfere with other pumps.

In step 608, the user activates the remote controller, which transmits the necessary instructions to the controller.

In step 610, the controller 504 processes the instructions and the pump device 10 is activated.

In step 612, the drive mechanism 508 rotates the reservoir 510 according to the required instructions and the infusion process commences.

In step 614, the encoder 73 checks the rotation of the reservoir thereby ensuring that the required quantity of medicament is administered to the user for the required time interval.

Figure 27:
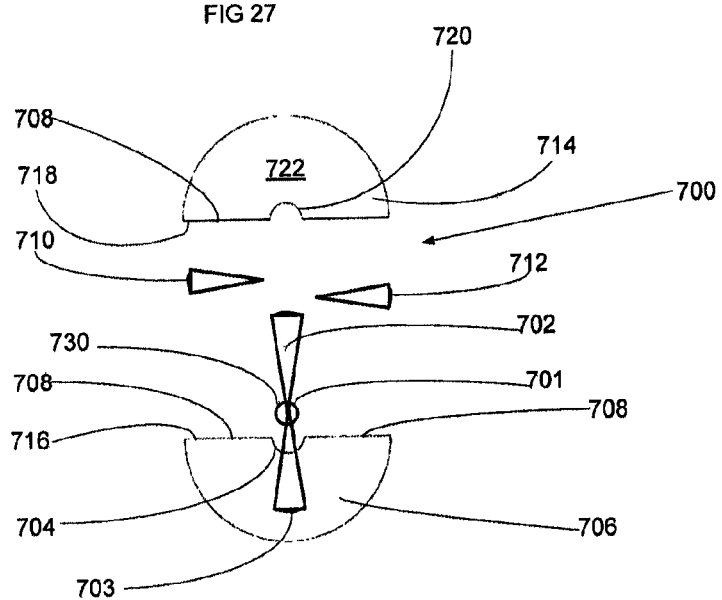
FIG. 27 presents an assembling process for constructing a reservoir by assembling its various elements, in accordance with a preferred embodiment of the present invention.

Reference is now made to FIG. 27, which shows an assembling process for constructing a reservoir 700 by assembling its various elements, in accordance with a preferred embodiment of the present invention. Initially, a central axle 701 is inserted into an upper cutout 704 located on an upper surface 703 and a corresponding lower cutout (not shown) located on a lower surface (not shown) of a first portion 706 of the reservoir 700, such that the stationary arm 702 is in a transverse relationship to a diameter 708.

Rotating arm 710 and 712 are inserted into the first portion 706 such that the arms 710 and 712 are partially located within the first portion 706.

A second portion 714 of the reservoir 700 including, inter alia an upper cutout 720 located on an upper surface 722 of the second portion 714 and a lower cutout (not shown) located on a lower surface (not shown) of the second portion 714, is bonded to the first portion 706. The central axle 701 is inserted into the upper and lower cutouts of the second portion 714, thereby sealing the stationary arms and the rotating arms within the reservoir 700 and permitting free rotation of the reservoir 700 and the rotating arm 702 relative to the stationary arms 710 and 712.

Thus, the rotational travel of the rotating arms does cross an assembling line between the first portion 706 and the second portion 714 and leakage from the reservoir 700 is prevented.

It is further appreciated that the portions 706 and 714 are constructed from plastic material such that the stationary arms 702 do not cross and/or bypass parting lines 716 and 718, thus preventing leakage from the reservoir 700.

It is shown in FIG. 27 that the outer surfaces of the reservoir 700, the rotating arm 702, the central axle 701 and the stationary arms 710 and 712 are contoured permitting smooth and uninterrupted rotation of the reservoir 700 and the rotating arm 702 relative to the stationary arms 710 and 712. In order to enable smooth rotation thereof, these outer surfaces are coated with a sealant material 730, such as rubber, Silicone rubber, polymerized siloxanes, polysiloxanes, WKT and Polydimethylsiloxane and/or any combination thereof.

It is appreciated that during operation of the reservoir 700, the sealant material 730 undergoes compression due to the size and shape of the members of the reservoir 700. Thus, the thickness and mechanical strength of the sealant material 730 must be selected so as to prevent leakage and seepage of the fluid and replacement air, as described above, from the reservoir 700.

Additionally, the surfaces of the central axle 701, the rotating arm 702 and the stationary arms 710 and 712 are smooth, curve-contoured and uninterrupted by corners, acute changes in the radii of curvature and parting lines.

Figure 28:
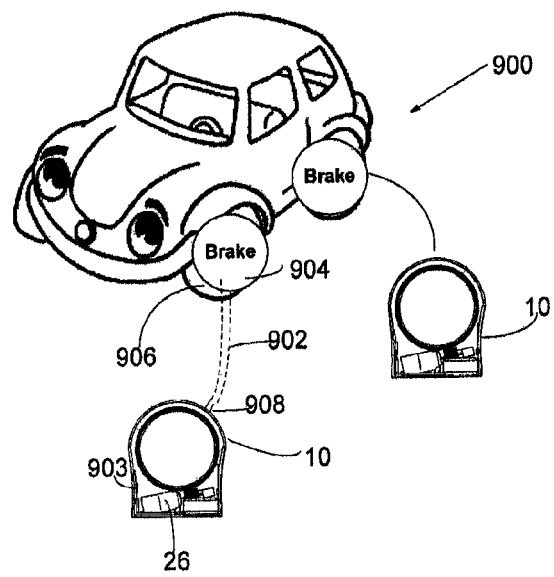
FIG. 28 shows the use of the pump for a non-medical use, such as in the breaking system of motor-car, in accordance with a further preferred embodiment of the present invention.

Reference is now made to FIG. 28, which shows a non-medical use of the pump device 10, such as in the hydraulic braking system of a motor-vehicle 900, in accordance with yet another preferred embodiment of the present invention. FIG. 28 shows that an exit conduit 902 is a controller 903 of a fluid pump 905, which is fluidly coupled to an inlet 904 of the hydraulic brake of a vehicle wheel 906, providing the required braking power for the vehicle 900.

In operation, when the driver applies foot pressure to the brake pedal (not shown), an electronic signal is transmitted to the controller 903 thereby operating the braking brake 904.

What is claimed is:

1. A medicament reservoir, comprising:
a reservoir configured to contain a fluid-medicament, the reservoir includes at least one stationary arm and at least one rotating arm, wherein said at least one rotating arm is attached to an inner wall of said reservoir, wherein said at least one rotating arm is rotated relative to said at least one stationary arm such that at least one predetermined dosage of said medicament is impelled through one medicament channel attached to said reservoir and infuses said medicament into a user, wherein an operating device is configured to rotate said at least one rotating arm, said operating device comprises a drive mechanism, said drive mechanism is at least one of a mechanical drive mechanism and an electromechanical drive mechanism; and
an encoder attached to the reservoir, wherein the encoder is configured to determine an angular rotation of the reservoir, thereby ensuring a closed-loop control for the reservoir to allow an exact quantity of said at least one dose of medicament to infuse into the user, wherein the encoder includes at least a plurality of graduation marks, wherein the accuracy of said angular rotation is determined by the accuracy of a location of said graduation marks.

2. The reservoir of claim 1, wherein said at least one stationary arm comprises a proximal end and a distal end, said proximal end is attached to a central axle of said reservoir and said distal end abutting said reservoir, and wherein said at least one rotating arm comprises a proximal end and a distal end and wherein said proximal end abuts said central axle and said distal end is attached to said reservoir.

3. The reservoir of claim 2, wherein said medicament channel is located within said at least one stationary arm.

4. The reservoir of claim 2, wherein said medicament channel is located within said at least one rotating arm.

5. The reservoir of claim 2, wherein each of said at least one rotating arm and said at least one stationary arm extends diametrically through said central axle, thereby partitioning said reservoir into at least two compartments.

6. The reservoir of claim 5, wherein said least two compartments store different medicaments.

7. The reservoir of claim 1, wherein said reservoir comprises a replacement air input channel thereby replacement air flows into said reservoir to replace said dispensed medicament.

8. The reservoir of claim 1, wherein said drive mechanism is mechanically coupled to said reservoir and rotates said reservoir about a central axle and further rotates said at least one rotating arm within said reservoir, thereby impelling said fluid out of said reservoir.

9. The reservoir of claim 1, wherein said reservoir has an ellipsoidal-contoured leakage-proof fluid outer wall.

10. The reservoir of claim 1, wherein said medicament outlet is fluidly coupled to a syringe needle for infusing said at least one predefined dosage medicament into said user.

11. The reservoir of claim 1, wherein said reservoir is at least one of disposable, detachable, and reusable.

12. A method of assembling a reservoir utilized in a compact fluid infusion pump, comprising:

providing a first portion of a semi-circular leakage-proof fluid reservoir having a contoured outer wall and an upper cutout and a lower cutout;

providing a second portion of a semi-circular leakage-proof fluid reservoir having a contoured outer wall and an upper cutout and a lower cutout;

attaching at least one rotating arm to said first portion of the semi-circular leakage-proof fluid reservoir;

attaching at least one stationary arm to a contoured central axle;

inserting said contoured central axle and said at least one stationary arm into the reservoir by inserting said central axle into said upper cutout and said lower cutout located in said first portion;

inserting said at least one rotating arm into said first portion;

rotating said at least one rotating arm into said second portion; and bonding said first portion and said second portion.

13. The method of claim 12, wherein said central axle, said at least one rotating arm and said at least one stationary arm are coated with a compressible sealant material on said central axle.

14. The method of claim 13, wherein said at least one rotating arm and said first portion of said semi-circular leakage-proof fluid reservoir are integrated.

* * * * *